United States Patent [19]

Aktogu et al.

[11] Patent Number: 5,093,337
[45] Date of Patent: * Mar. 3, 1992

[54] SUBSTITUTED DERIVATIVES OF 20,21-DINOREBURNAMENINE, THEIR USE AS MEDICAMENTS AND THE PHARMACEUTICAL COMPOSITIONS CONTAINING THEM

[75] Inventors: Nurgün Aktogu, Le Plessis-Robinson; Francois Clémence; Claude Oberlander, both of Paris, all of France

[73] Assignee: Roussel Uclaf, Paris, France

[*] Notice: The portion of the term of this patent subsequent to Jul. 23, 2008 has been disclaimed.

[21] Appl. No.: 391,511

[22] PCT Filed: Nov. 16, 1988

[86] PCT No.: PCT/FR88/00562

§ 371 Date: Jul. 18, 1989

§ 102(e) Date: Jul. 18, 1989

[87] PCT Pub. No.: WO89/04830

PCT Pub. Date: Jun. 1, 1989

[30] Foreign Application Priority Data

Nov. 19, 1987 [FR] France .................. 87 15980

[51] Int. Cl.$^5$ .................. A61K 31/445; C07D 461/00
[52] U.S. Cl. ...................... 514/283; 546/51
[58] Field of Search ............. 546/51; 514/283

[56] References Cited

U.S. PATENT DOCUMENTS

| | | | |
|---|---|---|---|
| 3,755,335 | 8/1973 | Thal et al. | 546/51 |
| 4,045,443 | 8/1977 | Pfäffli | 546/51 |
| 4,291,038 | 9/1981 | Farcilli et al. | 546/51 X |
| 4,356,305 | 10/1982 | Szántay et al. | 546/51 |
| 4,501,740 | 2/1985 | Clemence et al. | 514/283 |

FOREIGN PATENT DOCUMENTS

| | | | |
|---|---|---|---|
| 2703920 | 8/1977 | Fed. Rep. of Germany | 546/51 |
| 2339618 | 9/1977 | France | 546/51 |
| 2381048 | 9/1978 | France . | |
| 2590572 | 5/1987 | France . | |
| 2106908 | 4/1983 | United Kingdom | 546/51 |
| 2107317 | 4/1983 | United Kingdom . | |

Primary Examiner—Diana G. Rivers
Attorney, Agent, or Firm—Bierman and Muserlian

[57] ABSTRACT

The invention concerns compounds of formula (I);

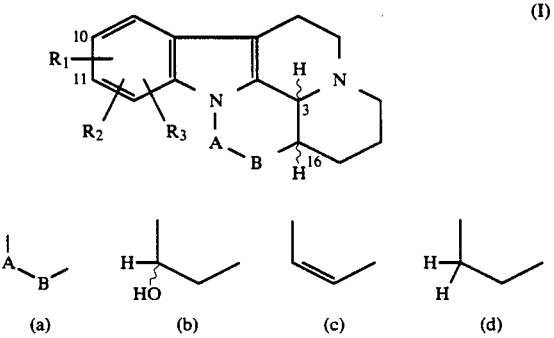

in which $R_1$, $R_2$ and $R_3$, identical or different, stand for hydrogen, halogen, alkyl or alkoxy ($C_{1-5}$), hydroxy, trifluoromethyl, nitro, amino, alkylamino, dialkylamino, acylamino, $R_1$, $R_2$ and $R_3$ being unable to stand for hydrogen simultaneously and in which (a) stands for (b), (c), or (d), all possible isomeric forms of said products of formula (I) being racemic or optically active, as well as their additional salts with acids, their preparation and the new intermediate products obtained, their application as drugs in particular nootropes, antidepressants, neuronal protectors, anti-anoxics, anti-ischemics, and the compositions containing them.

14 Claims, No Drawings

SUBSTITUTED DERIVATIVES OF 20,21-DINOREBURNAMENINE, THEIR USE AS MEDICAMENTS AND THE PHARMACEUTICAL COMPOSITIONS CONTAINING THEM

The invention relates to new substituted derivatives of 20,21-dinoreburnamenine, their preparation process and the new intermediates thus obtained, their use as medicaments and the pharmaceutical compositions containing them.

A subject of the invention is new compounds of formula (I):

in which $R_1$, $R_2$ and $R_3$, identical or different, represent a hydrogen atom, a halogen atom, an alkyl or alkoxy radical containing from 1 to 5 carbon atoms, a hydroxy, trifluoromethyl, nitro, amino, alkylamino or dialkylamino radical in which the alkyl radical contains from 1 to 5 carbon atoms, an acylamino radical in which the acyl radical represents the remainder of an aliphatic acid containing up to 6 carbon atoms, $R_1$, $R_2$ and $R_3$ not being able, at the same time, to represent a hydrogen atom and in which the group:

represents either:

the said products of formula (I) being in all the possible racemic or optically active forms, as well as the addition salts with mineral or organic acids of the said product of formula (I).

In the products of formula (I), the hydrogen atom in position 3 and the hydrogen atom in position 16 can each occupy one or other of the alpha and beta orientations, which determines the existence of cis and trans diastereoisomers. Also, the hydroxy radical in position 14 can be in alpha or beta form, when the group:

represents in the products of formula (I).

When $R_1$, $R_2$ and $R_3$ represent an alkyl radical, it is preferred to be a methyl, ethyl, n-propyl or isopropyl radical, but these substituents can also represent an n-butyl, isobutyl or n-pentyl radical.

When $R_1$, $R_2$ and $R_3$ represent an alkoxy radical, it is preferred to be a methoxy or ethoxy radical, but they can also represent a linear, secondary or tertiary propoxy, isopropoxy or butoxy radical.

When $R_1$, $R_2$ and $R_3$ represent a halogen atom, it is preferred to be a chlorine atom, but they can also represent a fluorine, bromine or iodine atom.

When $R_1$, $R_2$ and $R_3$ represent an alkylamino radical, it is preferred to be a methylamino, ethylamino or propylamino radical.

When $R_1$, $R_2$ and $R_3$ represent a dialkylamino radical, it is preferred to be a dimethylamino or diethylamino radical.

When $R_1$, $R_2$ and $R_3$ represent an acylamino radical, it is preferred to be an acetylamino, propionylamino or butyrylamino radical.

The addition salts with mineral or organic acids of the products of formula (I) can be, for example, the salts formed with the following acids: hydrochloric, hydrobromic, hydriodic, nitric, sulphuric, phosphoric, propionic, acetic, formic, benzoic, maleic, fumaric, succinic, tartaric, citric, oxalic, glyoxylic, aspartic, ascorbic; alkylmonosulphonic acids such as methanesulphonic acid, ethanesulphonic acid, propanesulphonic acid; alkyldisulphonic acids such as methanedisulphonic acid, alpha,beta-ethanedisulphonic acid; arylmonosulphonic acids such as benzenesulphonic acid; and aryldisulphonic acids.

A subject of the invention is in particular the compounds of formula (I) characterized in that $R_1$, $R_2$ and $R_3$, identical or different, represent a hydrogen atom or a methyl, ethyl, methoxy or ethoxy radical, a chlorine atom, a hydroxy, trifluoromethyl or nitro radical, in all the possible racemic or optically active isomer forms, as well as the addition salts with mineral or organic acids.

A subject of the invention is also in particular the compounds of formula (I) characterized in that one of the three substituents $R_1$ or $R_2$ or $R_3$ represents, in position 10 or 11, a methyl, ethyl, methoxy or ethoxy radical, a chlorine atom, a hydroxy, trifluoromethyl or nitro radical, the two other substituents representing a hydrogen atom, in all the possible racemic or optically active isomer forms, as well as the addition salts with mineral or organic acids.

The invention also relates in particular to the compounds of formula (I) characterized in that two of the three substituents $R_1$, $R_2$ or $R_3$ represent, in position 9, 10 or 11, a chlorine atom, a methyl, ethyl, methoxy or ethoxy radical, the third substituent representing a hydrogen atom, or in that $R_1$, $R_2$ and $R_3$ represent, all three in these positions, a chlorine atom or a methyl, ethyl, methoxy or ethoxy radical, in all the possible racemic or optically active isomer forms, as well as the addition salts with mineral or organic acids.

A subject of the invention is quite particularly the compounds of formula (I) characterized in that the hydrogen atom in position 3 and the hydrogen atom in position 16 are trans, in all the possible racemic or optically active isomer forms, as well as the addition salts with mineral or organic acids and those characterized in that the group $$\overset{|}{A}\diagdown_{B}\diagup$$

represents either

[structure with OH], or [structure with double bond]

in all the possible racemic or optically active isomer forms, as well as the addition salts with mineral or organic acids.

The preferred compounds of formula (I) of the invention are those of which the names follow:

[(+) (14alpha, 16alpha)]-14,15-dihydro-10-methoxy-20,21-dinoreburnamenin-14-ol,
[(±) (14alpha, 16alpha)] (14,15-dihydro-11-methyl-20,21-dinoreburnamenin-14-ol,
[(±) (16alpha)]-11-chloro-20,21-dinoreburnamenine,
[(±) (16alpha)]-11-methoxy-20,21-dinoreburnamenine,
[(±) (16alpha)]-11-methyl-20,21-dinoreburnamenine, as well as their addition salts with mineral or organic acids.

The invention also relates to a process for the preparation of compounds of formula (I) characterized in that a compound of formula (II):

[Structure (II) with $R_1$, $R_2$, $R_3$ substituents]

in which $R_1$, $R_2$ and $R_3$ have the significances already indicated, is reduced so as to obtain a compound of formula ($I_A$) corresponding to a product of formula (I) in which:

$$\overset{|}{A}\diagdown_{B}\diagup$$

represents

[structure with H and HO]

the said compound of formula ($I_A$) being, if desired, dehydrated so as to obtain a corresponding compound of formula ($I_B$), representing a compound of formula (I) in which:

$$\overset{|}{A}\diagdown_{B}\diagup$$

represents

[double bond structure]

the said compound of formula ($I_B$) being, if desired, reduced to a corresponding compound of formula ($I_C$) representing a compound of formula (I) in which:

$$\overset{|}{A}\diagdown_{B}\diagup$$

represents

[structure with H, H]

and if desired all the said products of formula (I) obtained are treated with a mineral or organic acid in order to form the salt.

In the preferred conditions for putting the invention into operation, the process above is carried out in the following way:

the reduction of the compounds of formula (II) to a compound of formula ($I_A$) in which:

$$\overset{|}{A}\diagdown_{B}\diagup$$

represents

[structure with H and HO]

is carried out with a hydride, in particular a mixed hydride, such as for example mixed hydride of lithium and aluminium, diethylhydride of sodium and aluminium, sodium hydroboride, lithium hydroboride, or diisobutylaluminium hydride.

The dehydration agent used in order to obtain, starting from compounds of formula ($I_A$), the compounds of formula ($I_B$) in which:

$$\overset{|}{A}\diagdown_{B}\diagup$$

represents

[double bond structure]

is an acid such as hydrochloric acid, hydrobromic acid, sulphuric acid, acetic acid, paratoluene sulphonic acid, methanesulphonic acid or a derivative of this acid such as copper trifluoromethane sulphonate, used in a catalytic quantity.

The product of formula (I$_B$) in which R$_1$, R$_2$ or R$_3$ represents an acylamino radical can be submitted, if appropriate, to a basic hydrolysis so as to eliminate the acyl group.

The base which is used is preferably a mineral base such as sodium or potassium hydroxide.

The reducing agent to which the compounds of formula (I$_B$) are submitted so as to obtain the compounds of formula (I$_C$) in which

represents

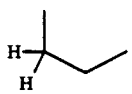

is hydrogen in the presence of a catalyst such as platinum or palladium.

The products of formula (I) for which the hydrogen atom in position 3 and the hydrogen atom in position 16 are in cis or trans position, are obtained from products of formula (II) which have the corresponding stereochemical form.

The product of formula (I) in which

represents

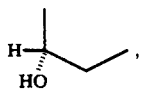

OH being in axial position, is obtained by epimerization in an acid medium of the product of formula (I) in which:

represents

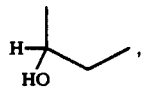

OH being in equatorial position.

The optically active forms of the products of formula (I) can be prepared by resolution of the racemics according to the usual methods, either by resolving the racemic product of formula (II) so as to obtain a product of formula (II') 3alpha and a product of formula (II'') 16alpha which are submitted to the reduction and dehydration reactions indicated above, so as to obtain the products of formulae (I'$_A$), (I'$_B$), (I'$_C$) corresponding respectively to the products (I$_A$), (I$_B$), (I$_C$) 3alpha and the products (I$_A$), (I$_B$), (I$_C$) corresponding respectively to the products (I$_A$), (I$_B$), (I$_C$) 16alpha, or by directly resolving the racemic products of formula (I).

An optically active compound is preferably used such as (+) (−) di-O,O′-pivaloyl D- or L-tartaric acid.

The compounds of formula (I) as defined above as well as their addition salts with acids show interesting pharmacological properties.

Some products show in particular an affinity for alpha-2 adrenergic receptors.

Some products can also show interesting nootrope properties (anti-amnesic effect and reversion from an amnesic deficit after injury to a septal cholinergic deficit), anti-depressive, neuronal protective, anti-anoxic and anti-ischemic properties.

The properties justify their use in therapeutics and a subject of the invention is also, as medicaments, the products as defined by the formula (I) above, the said products of formula (I) being in all the possible racemic or optically active isomer forms, as well as the addition salts with pharmaceutically acceptable mineral or organic acids of the said products of formula (I).

A subject of the invention is more particularly, as medicaments, the following products (I):

[(±) (14alpha, · 16alpha)]-14,15-dihydro-10-methoxy-20,21-dinoreburnamenin-14-ol,
[(±) (14alpha, 16alpha)]-14,15-dihydro-11-methyl-20,21-dinoreburnamenin-14-ol,
[(±) 16alpha]-11-chloro-20,21-dinoreburnamenine,
[(±) 16alpha]-11-methoxy-20,21-dinoreburnamenine,
[(±) 16alpha]-11-methyl-20,21-dinoreburnamenine, as well as their addition salts with pharmaceutically acceptable mineral or organic acids.

The medicaments, which are a subject of the invention, can be used in the treatment of cerebral insufficiencies of anoxic or ischemic origin, in disorders of the memory and of the attention. They can also be used as anti-depressants.

The invention extends to pharmaceutical compositions containing as active principle the medicaments defined above.

These pharmaceutical compositions can be administered by oral or rectal route, by parenteral route or by local route as a topical application on the skin and the mucosa.

These compositions can be solid or liquid and are presented in the pharmaceutical forms currently used in human medicine, such as, for example, plain or sugar-coated tablets, gelules, granules, suppositories, injectable preparations, ointments, creams, gels and aerosol preparations; they are prepared according to the usual methods. The active principle can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The usual posology, variable according to the product used, the patient being treated and the affection in question, can be, for example, from 10 to 200 mg per day in an adult, by oral route.

A subject of the invention is also, as new chemical products, necessary for the preparation of products of formula (I), the products of formula (II) with the exception of products of formula (II$_A$):

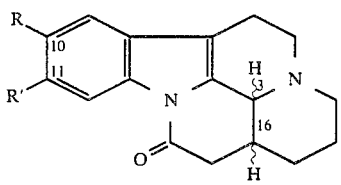

for which R and R', identical or different, represent a hydroxy or methoxy radical.

The products of formula (II$_A$) correspond to certain products of formula (I) of Belgian Patent No. 764166.

The products of formula (II) can present some of the pharmacological properties indicated previously for the products of formula (I).

The products of formula (II) are prepared according to the process given in French Patent No. 2168853 for deethyleburnamonine, starting with 2,3,4,6,7,12-hexahydro indolo(2,3-a)quinolizine of formula:

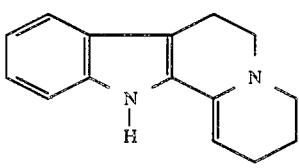

the substituted derivatives of the 20,21-dinoreburnamenine of the present invention are therefore prepared from substituted derivatives corresponding to 2,3,4,6,7,12-hexahydro indolo(2,3-a)quinolizine.

Another process for the preparation of products of formula (II) consists of submitting a product of formula:

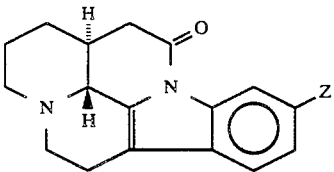

in which Z represents a hydrogen atom, to a nitration reaction, so as to obtain a product of formula (II$_A$):

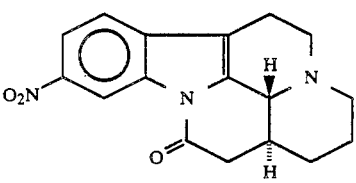

which is reduced, if appropriate, so as to obtain a product of formula (II$_B$):

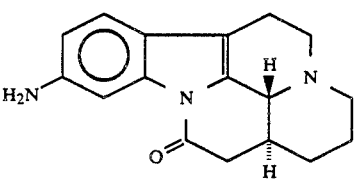

which if appropriate, either is submitted to an alkylation or acylation reaction, or is converted into diazonium salt, starting from which the derivatives of formula (II$_C$):

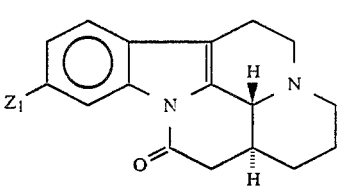

in which Z$_1$ represents a hydroxy radical or a halogen atom, are prepared by known processes, which are converted if appropriate into corresponding derivatives in which Z$_1$ represents an alkoxyl or alkyl radical.

Corresponding examples for the preparation of the product of formula (II) are given hereafter in the experimental part.

The examples given hereafter illustrate the invention without however limiting it.

EXAMPLE 1

[(±) (14alpha, 16alpha)]-11-chloro-14,15-dihydro-20,21-dinoreburnamenin-14-ol (trans, dl)

A solution of 4.6 g of (±) (16alpha) 11-chloro-20,21-dinoreburnamenin-14(15H)-one in 50 cm$^3$ of toluene is cooled to $-10°$ C., and 12 cm$^3$ of a 2.36M solution of diethyl-aluminium-sodium dihydride in toluene is added slowly, maintaining the temperature of the medium at about $-5°$ C. After agitation at 0° C. for 30 minutes, water is added in order to destroy the excess reducing agent, then 100 cm$^3$ of water is added, and the suspension obtained is agitated for 16 hours. The suspension is separated, washed thoroughly with water until a neutral pH of the wash water is obtained, dried at 100° C. under reduced pressure, dissolved in a mixture of methylene chloride and methanol (2-1), filtered and brought to dryness. The residue is triturated with a methanol-5N sodium hydroxide mixture (100 cm$^3$–30 cm$^3$) and taken to reflux for 15 hours. The precipitate is separated, washed with water, triturated with methanol at reflux several times, dried and 2.5 g of expected product is obtained. m.p.=257° C.

NMR Spectrum (DMSO 250 MHz ppm):
isomer with axial OH
5.90: >C(H) OH
trace of isomer with equatorial OH (2%)
5.53: >C(H) OH

EXAMPLE 2

[(±) (16alpha)]-11-chloro-20,21-dinoreburnamenine (trans dl) and its neutral fumarate 1.9 g of [(±) (14alpha, 16beta)-11-chloro-14,15-dihydro-20,21-dinoreburnamenin-14-ol, 40 mg of paratoluene sulphonic acid in 40 cm$^3$ of toluene are taken to reflux for 15 hours. After filtering, the insoluble part is washed with methylene chloride and the filtrate is concentrated to dryness. The residue is chromatographed on silica, eluted with an ethyl acetate-methylene chloride mixture (1-1) and 1.2 g of expected product is obtained. m.p.=118° C.

1.16 g of the latter is dissolved in 50 cm$^3$ of anhydrous ethanol, 472 mg of fumaric acid is added, maintaining under agitation for 3 hours. After separation and recrystallization from ethanol, 1.06 g of neutral fumarate is obtained. m.p.=215° C.

NMR Spectrum (CDCl₃ 250 MHz ppm):
(base)

| | |
|---|---|
| 5.11 (dd) J = 2 and 7.5: | ethylene H in beta position of the indole |
| 6.88 (dd) J = 3 and 7.5: | ethylene H in alpha position of the indole |
| 7.05 (dd) J = 2 and 8.5: | H₅ ⎫ |
| 7.30 (d, J = 2): | H₇ ⎬ indole |
| 7.34 (d, J = 8.5): | H₄ ⎭ |
| 1.3 to 3.2 the other protons | |

EXAMPLE 3

[(±) (14beta)]-10-chloro-14,15-dihydro-20,21-dinoreburnamenin-14-ol (cis, dl)

5.5 g of (±) 10-chloro-20,21-dinoreburnamenin-14(15H)-one in 50 cm³ of toluene is cooled to 0° C. and 14 cm³ of a solution of diethyl-aluminium-sodium dihydride is added drop by drop, with agitation for one hour at 0° C. Then 50 cm³ of water is added very slowly at 0° C. and agitation of the suspension obtained is continued for one hour. After separating and washing thoroughly with water, 4.73 g of crude product is obtained. m.p.=244° C.

2.4 g of this product is recrystallized from 50 cm³ of tetrahydrofuran, cooled to −20° C., separated and dried under reduced pressure, and 1.7 g of product is obtained, m.p.=251° C.

This product is taken up with a methylene chloride-methanol mixture, filtered, and brought to dryness. The solid obtained is washed with 50 cm³ of methanol. After drying at 70° C. under reduced pressure, 1.42 g of product is obtained (equatorial OH) m.p.=252° C.

NMR Spectrum (DMSO 250 MHz ppm):

Crude product = mixture containing 10 to 15% of axial OH for 85 to 90% of equatorial OH 5.54 (dt):  axial —OH   0.63 (m): 1H 5.90 (m):  equatorial —OH   1.3 to 3.2: the other protons 4.17 and 4.11:  cis junction —N 6.48 (d): OH
7.06 (dd): H₆ indole
7.41 (d): H₄ indole
7.66 (d): ⎫ H⁷ indole
7.50 (d): ⎭

EXAMPLE 4

[(±) (14alpha, 16alpha)]-10-chloro-14,15-dihydro-20,21-dinoreburnamenin-14-ol (trans, dl)

7.5 g of [(±) (16alpha)]-10-chloro-20,21-dinoreburnamenin-14(15H)-one is dissolved in 100 cm³ of toluene and 19.5 cm³ of a solution (1.8M) of diethyl-aluminium-sodium dihydride in toluene is added drop by drop at 0° C. The mixture is then maintained under agitation at 0° C. for one hour. Water is then added very slowly without rising above 5° C. and agitation is maintained for a quarter of an hour. The precipitate is separated, washed thoroughly with water, dried under reduced pressure at 70° C. and 7.46 g of crude product is obtained, corresponding to the isomer with equatorial OH. 3 g of the latter is put in suspension in 30 cm³ of N hydrochloric acid and agitated for 15 hours at ambient temperature. The pH is brought to 10 by addition of sodium hydroxide, followed by separation and washing with water. 2.8 g of product is obtained. After two recrystallizations from tetrahydrofuran, 760 mg of expected product is obtained. The mother-liquors are concentrated to dryness; the residue is treated with N hydrochloric acid, alkalized and recrystal-lized as previously and 1.03 g of expected product is recovered.

NMR Spectrum (DMSO, 250 MHz, ppm):
equatorial OH
5.89 (m): >C(H) equatorial OH
6.27 (d, J=7): axial OH
7.05 (d, d, J=2 and 8.5): H₆-indole
7.39 (d, J=2): H₄-indole
7.44 (d, J=8.5): H₇-indole
1.1 to 3.1: the other protons

EXAMPLE 5

Hemifumarate of [(±) 16alpha]-10-chloro-20,21-dinoreburnamenine (trans d,l)

A suspension is prepared with 6 g of [(±) (14alpha, 16alpha)]-10-chloro-14,15-dihydro-20,21-dinoreburnamenin-14-ol in 100 cm³ of toluene. 300 mg of paratoluene-sulphonic acid is added in one go and the whole is taken to reflux for 10 hours. After cooling to ambient temperature, the insoluble part is separated and washed with ethyl acetate, and the filtrate is brought to dryness. The residue is triturated in 50 cm³ of a sodium bicarbonate solution, separated, washed thoroughly with water and dried under reduced pressure, followed by chromatography on silica by eluting with a methylene chloride-methanol mixture (97-3) and 3.9 g of product is isolated in the form of a base. m.p.=151° C.

1.5 g of the latter is dissolved in an ethyl acetate-isopropanol mixture (8-2), 305 mg of fumaric acid is added and agitation is maintained for one hour 30 minutes at ambient temperature. After separating, washing with 50 cm³ of ethyl acetate and then with 25 cm³ of isopropanol, and drying under reduced pressure at 70° C., 1.57 g is obtained. m.p.=241° C.

NMR Spectrum (CDCl₃ 250 MHz, ppm):
5.10 (d,d) J=2 and 7.5: ethylene H's in beta position of N
6.89 (d,d) J=3 and 7.5: ethylene H's in alpha position of N
7.09 (d,d) J=2 and 8.5: H₆ indole
7.2 (d, J=8.5): H₇ indole
7.41 (d, J=2): H₄ indole
1.3 to 3.2: the other protons

EXAMPLE 6

Hemifumarate of (±) 10-chloro-20,21-dinoreburnamenine (cis dl)

1.6 g of [(±) (14beta)]-10-chloro-14,15-dihydro-20,21-dinoreburnamenin-14-ol is dissolved in 20 cm³ of acetic acid and taken to reflux for 2 hours. The solution is concentrated, water is added and it is alkalized to pH 10 with concentrated sodium hydroxide. The precipitate obtained is extracted with methylene chloride and the organic phase is washed with water and dried. The solvents are eliminated and the residue is triturated several times in 50 cm³ of xylene, followed by concentration under reduced pressure at 80° C. The residue is chromatographed on silica by eluting with a methylene chloride-methanol mixture (95-5) and 1.01 g of product is isolated in the form of a base. 1 g of the latter is dissolved in an ethyl acetate-isopropanol mixture (20-10), 204 mg of fumaric acid is added, with agitation for 48 hours at ambient temperature. After separation, washing is carried out with 10 cm³ of isopropanol and then with 20 cm³ of ethyl acetate. After drying under reduced pressure at 70° C., 750 mg of expected product is obtained. m.p.=188° C.

NMR Spectrum (DMSO 250 MHz ppm):
4.53 (m): CH-cis junction N
5.41 (d,d, Jr 6 and 8): CH=CH—N
7.31 (d, Jr 8)): N—CH=CH
7.14 (d,d, J=2.5 and 9): H₆ indole
7.48 (d, J=2.5): H₄ indole
7.61 (d, J approx. 9): H₇ indole
0.6 to 3.3: the other protons
6.6 (s): ethylene H's of the fumaric acid

EXAMPLE 7

[(±) (14beta, 16alpha)]-14,15-dihydro-11-methyl-20,21-noreburnamenin-14-ol (trans d,l)

The operation is carried out as in example 1 starting with 2.1 g of [(±) 16alpha]-11-methyl-20,21-dinoreburnamenin-14(15H)-one. After introduction of the reagent, agitation is maintained for one hour at 0° C.; then 50 cm³ of water is added very slowly, with further agitation for one hour at 0° C. The precipitate is separated, washed thoroughly with water and dried at 80° C. under reduced pressure. 1.7 g of product is obtained which is dissolved in a methylene chloride-methanol mixture (2-1). After filtering, the filtrate is brought to dryness. The residue is triturated in 200 cm³ of methanol and dried, and 1.1 g of product is obtained. m.p. approx. 255° C.

NMR Spectrum (DMSO 250 MHz ppm):
possible equatorial OH
2.38 (s): CH₃—φ
5.46 (dt) (J=9 and 5.5): C H axial —OH
6.37 (d) (J=9): equatorial OH
6.84 (d,d) (J=8 and 1): H₅ indole
7.24 (d, J=8): H₄ indole
7.46 (wide S): H₇ indole
1.1 to 3.0: the other protons

EXAMPLE 8

[(±) (14alpha, 16alpha)]-14,15-dihydro-11-methyl-20,21-dinoreburnamenin-14-ol (trans, dl)

3.8 g of [(±) (14beta, 16alpha)]-14,15-dihydro-11-methyl-20,21-dinoreburnamenin-14-ol is put in suspension in 100 cm³ of 0.5N hydrochloric acid, under agitation and inert atmosphere, for 24 hours. 800 cm³ of water is added at 40° C. so as to make the hydrochloride soluble, and the mixture is alkalized by the addition of 20% ammonia. After agitating for a quarter of an hour, the precipitate is separated, washed thoroughly with water up to a neutral pH of the wash water and dried under reduced pressure at 70° C. 3.3 g of expected product is obtained. m.p.=232° C.

NMR Spectrum (DMSO 250 MHz ppm):
2.39 (s): CH₃φ
5.85:

equatorial OH
6.83: H₅ indole
7.23: H₄ and H₇ indole
6.08: axial OH

EXAMPLE 9

[(±) (14beta)]-14,15-dihydro-11-methyl-20,21-dinoreburnamenin-14-ol (cis, dl)

The operation is carried out as in example 1 starting with 9.7 g of (±) 11-methyl-20,21-dinoreburnamenin-14(15H)-one, with agitation for one hour after the introduction of the reagent. Water is added very slowly at 0° C. so as to destroy the excess reducing agent, then 100 cm³ of water is added, with agitation for 3 hours at ambient temperature. After separating, the precipitate is washed thoroughly up to a neutral pH of the wash water and 8.11 g of crude product is obtained. 3 g of the latter is dissolved in 100 cm³ of a methylene chloride-methanol mixture (2-1). After filtering, the filtrate is brought to dryness. The residue is recrystallized from 60 cm³ of ethyl acetate, separated, dried under reduced pressure at 70° C. and 1.63 g of expected product is obtained. m.p.=200° C.

| NMR Spectrum (DMSO 250 MHz ppm): |
| --- |
| equatorial OH 4.15 (d): —CH—N |
| 5.49 (m): —C(H) axial —OH |
| 6.29 (d): equatorial OH |
| 6.84 (d): H₅ ⎫ 7.25 (d): H₄ ⎬ indole 7.48: H₇ ⎭ |
| 2.39 (s): =CMe |
| 1.16 to 3.14 (m): other protons |

EXAMPLE 10

Fumarate of [(±) (16alpha)]-11-methyl-20,21-dinoreburnamenine (trans d,l)

The operation is carried out as in example 2 starting with 6.8 g of [(±) (14beta, 16alpha)](±) 14,15-dihydro-11-methyl-20,21-dinoreburnamenin-14-ol, taking to reflux for 8 hours and eluting with a methylene chloride-methanol mixture (95-5). 4.8 g of product is isolated in the form of a base. m.p.=130° C. 1.2 g of the latter is dissolved in an isopropanol-ethyl acetate mixture (50 cm³—50 cm³), 527 mg of fumaric acid is added and the whole is agitated for 16 hours at ambient temperature. The precipitate is separated, washed with 40 cm³ of isopropanol, dried at 80° C. under reduced pressure and 1.38 g of expected product is obtained. m.p. >260° C.

NMR Spectrum (CDCl₃ 250 MHz ppm): (base)
possible structure with trans junction
1.41 to 3.17: the CH₂ and CH
5.05 (d,d J=2 and 7): C(H)=CH—N
6.91 to 6.96: H₅ and the other =CH
7.13: H₇ indole
7.34: H₅ indole

EXAMPLE 11

Fumarate of (±) 11-methyl-20,21-dinoreburnamenine (cis, dl)

The operation is carried out as in example 2 starting with 5.33 g of [(±) (14beta)]-14,15-dihydro-11-methyl-20,21-dinoreburnamenin-14-ol, eluting with a methylene chloride-methanol mixture (93-7), and 5 g of product is isolated in the form of a base. m.p.=66° C. 2 g of the latter is dissolved in 100 cm³ of an isopropanol-ethyl acetate mixture (6-4), 439 mg of fumaric acid is added, with agitation for 16 hours. After separation and washing with 40 cm³ of ethanol, 1.89 g of expected product is obtained. m.p.=250° C.

| NMR Spectrum (CDCl₃ 250 MHz ppm): |
| --- |
| (base) |
| cis junction |
| 2.47 (s): CH₃-φ |
| 4.53 (m): 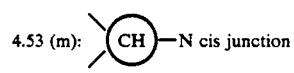 N cis junction |
| 5.29 (dd J=6 and 8): 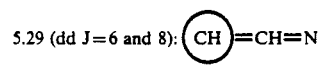 =CH=N |
| 6.92 (d J=8): N—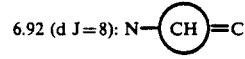=C |
| 6.94 (dd) J=8 and 1: H₅ <br> 7.13 (s): H₇ } indole <br> 7.35 (d J=8): H₄ |
| 0.8 to 3.4: the other protons |

EXAMPLE 12

Neutral fumarate of [(±) (16alpha)]-14,15-dihydro-11-methyl-20,21-dinor-eburnamenine (trans, dl)

2.9 g of [(±) (16alpha)]-11-methyl-20,21-dinoreburnamenine is hydrogenated in 90 cm³ of ethanol in the presence of platinum oxide for 2 hours. After filtering, the filtrate is brought to dryness and 3 g of product is obtained in the form of a base. m.p.=143° C. The operation is carried out as in example 2 starting with 2.87 g of the latter so as to obtain 2.83 g of expected fumarate. m.p.=235° C.

| NMR Spectrum (CDCl₃ 250 MHz ppm): |
| --- |
| (base) |
| 2.46: CH₃— |
| 3.65 (J = 11, 11 and 5): <br> 4.18 (J = 11–5.1): } CH₂ on N indole |
| 6.91: 1H <br> 7.03: 1H } aromatics |

| NMR Spectrum (CDCl₃ 250 MHz ppm): |
| --- |
| (base) |
| 7.34: 1H |

EXAMPLE 13

[(±) (14beta, 16alpha)]-14,15-dihydro-10-methyl-20,21-dinoreburnamenin-14-ol (trans, dl)

The operation is carried out as in example 3 starting with 2.6 g of [(±) (16alpha)]-10-methyl-20,21-dinoreburnamenin-14(15H)-one and 2.7 g of crude product is obtained. This is taken up with a methylene chloride-methanol mixture (2-1) and filtered; the filtrate is concentrated to dryness and the residue is washed with methanol. 2 g of expected product is obtained. m.p. >260° C.

| NMR Spectrum (DMSO 250 MHz ppm): |
| --- |
| trans junction with equatorial OH |
| 2.36 (s): CH₃ |
| 5.45 (dt, J=5.5–9.9): 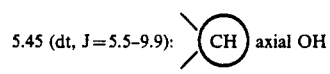 axial OH |
| 6.4 (d, J=9): equatorial OH |
| 7.15 (s): H₄ <br> 6.88 (d): H₆ } indole <br> 7.52 (d, J=8): H₇ |
| 1.1 to 3.0: the other protons |

EXAMPLE 14

[(±). (14beta)]-14,15-dihydro-10-methyl-20,21-dinoreburnamenin-14-ol (cis dl)

The operation is carried out as in example 3 starting with 7.9 g of (±) 10-methyl-20,21-dinoreburnamenin-14(15H)-one and 6.73 g of crude product is obtained. 3 g of the latter is dissolved in methylene chloride and filtered; the filtrate is brought to dryness and the residue is recrystallized from 65 cm³ of ethyl acetate. 2.13 g of expected product is obtained. m.p.=187° C.

NMR Spectrum (DMSO 250 MHz ppm):
cis junction, equatorial OH
2.36: CH₃
4.15: >CH—N
5.47: —C(H)—axial OH

EXAMPLE 15

[(±) (14alpha, 16alpha)]-14,15-dihydro-10-methyl-20,21-dinoreburnamenin-14-ol (trans, dl)

The operation is carried out as in example 8 starting with 2.2 g of [(±) (14beta, 16alpha)]-14,15-dihydro-10-methyl-20,21-dinoreburnamenin-14-ol, and 2 g of crude product is obtained which is recrystallized from 150 cm³ of tetrahydrofuran so as to isolate 850 mg of product with axial OH. After the mother-liquors are retreated, another 455 mg of product is recovered.

| NMR Spectrum (DMSO 250 MHz ppm): |
| --- |
| 2.36 (s): CH$_3$-φ |
| 5.86 (m): \C(H)/- equatorial OH |
| 6.10 (d, J=6.5): axial OH |
| 6.88 (d): H$_6$ ⎫ |
| 7.13 (s): H$_4$ ⎬ indole |
| 7.31 (d, J=8): H$_7$ ⎭ |
| 1.1 to 3.05: the other protons |

EXAMPLE 16

Hemifumarate of [(±) (16alpha)]-10-methyl-20,21-dinoreburnamenine (trans, dl)

The operation is carried out as in example 2 starting with 4.4 g of [(±) (14beta, 16alpha)]-14,15-dihydro-10-methyl-20,21-dinoreburnamenin-14-ol. The residue is chromatographed on silica, eluting with a methylene chloride-methanol mixture (97-3) and 3 g of product is obtained in the form of a base. m.p.=154° C.

1.4 g of this is dissolved in 80 cm$^3$ of an isopropanol-ethyl acetate mixture (1-1), 307 mg of fumaric acid is added, with agitation for 4 hours at ambient temperature. After separating, washing with ethyl acetate and then with isopropanol and drying under reduced pressure at 80° C., 1.3 g of expected product is obtained. m.p.=210° C.

| NMR Spectrum (CDCl$_3$ 250 MHz ppm): trans junction |
| --- |
| 1.42 to 3.18: the CH$_2$ and CH |
| 2.44: =C—Me |
| 5.05 (d,d J = 2 and 7): CH=CH—N |
| 6.94 and 6.98: ⎫ |
| 7.19 to 7.26: ⎬ aromatics and the other CH |

EXAMPLE 17

Fumarate of (±) 10-methyl-20,21-dinoreburnamenine (cis, dl)

The operation is carried out as in example 16 starting with 4.1 g of (±) 14alpha 14,15-dihydro-10-methyl-20,21-dinoreburnamenin-14-ol and 3.6 g of oily product is obtained. 1.508 g of the latter is dissolved in 50 cm$^3$ of isopropanol, 331 mg of fumaric acid is added and agitation is carried out for 5 hours at ambient temperature. After separating, washing with isopropanol and then with isopropyl ether, 1.16 g of expected product is obtained. m.p.=180° C.

| NMR Spectrum (CDCl$_3$ 250 MHz ppm): |
| --- |
| (base) |
| 2.44 (s): CH$_3$-φ |

| NMR Spectrum (CDCl$_3$ 250 MHz ppm): |
| --- |
| 4.53 (m): \C(H)/—N cis junction |
| 5.28 (dd, J=6.5 and 7.5): —(CH)=CH—N |
| 6.91 (d, J=7.5): N—(CH)=CH |
| 7.00 (d, J=8): H$_6$ ⎫ |
| 7.21 (d, J=8): H$_7$ ⎬ indole |
| 7.26 (s): H$_4$ ⎭ |
| 0.9 (m): 1H |
| 1.44 to 3.4: the other protons |

EXAMPLE 18

Hemifumarate of [(±) (16alpha)]-14,15-dihydro-10-methyl-20,21-dinoreburnamenine (trans, dl)

The operation is carried out as in example 12 starting with 1.6 g of [(±) (16alpha)]-10-methyl-20,21-dinoreburnamenine and 1.4 g of expected product is obtained in the form of a base. m.p.=146° C. Starting with 1.369 g of this and 298 mg of fumaric acid, and after recrystallization from ethanol, 0.84 g of expected fumarate is obtained. m.p.=254° C.

| NMR Spectrum (CDCl$_3$ 250 MHz ppm): trans junction |
| --- |
| 2.43: C H$_3$ -φ |
| 3.65 (dt): C(H)$_2$—N-indole |
| 4.18 (m): |
| 6.95 (d,d): H$_6$ ⎫ |
| 7.13 (d): H$_7$ ⎬ indole |
| 7.25: H$_4$ ⎭ |
| 1.22 (m): 1H |
| 1.5 to 3.2: 13H the other protons |

EXAMPLE 19

Hemifumarate of (±) 14,15-dihydro-10-methyl-20,21-dinoreburnamenine (cis, dl)

The operation is carried out as in example 12 starting with 2 g of (±) 10-methyl-20,21-dinoreburnamenine and 1.8 g of product is obtained in the form of a base, m.p.=138° C. 1.6 g of the latter is salified in 100 cm$^3$ of ethyl acetate and 50 cm$^3$ of isopropanol with 697 mg of fumaric acid so as to obtain, after crystallization from isopropanol, 1.55 g of expected product. m.p.=210° C.

| NMR Spectrum (CDCl$_3$ 250 MHz ppm): |
| --- |
| cis function |
| 2.46 (s): C(H$_3$)-φ |
| 3.73 (dt, J=5-11.5-12): CH$_2$—N-indole |
| 4.08(d,d J=6-11.5): |

NMR Spectrum (CDCl₃ 250 MHz ppm):

4.33 (m): 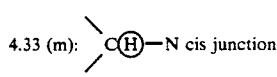 —N cis junction 7.0 (d): H₆
7.17 (d): H₇  } indole
7.28 (s): H₄

EXAMPLE 20

[(±) 14beta]-14,15-dihydro-11-methoxy-20,21-dinoreburnamenin-14-ol (cis, dl)

The operation is carried out as in example 3 starting with 3.5 g of (±) 11-methoxy-20,21-dinoreburnamenin-14(15H)-one and 8 g of isomer with equatorial OH is obtained. m.p.=230° C. 3.5 g of crude product is recrystallized from an ethyl acetate-isopropanol mixture (1-1) and 2 g of expected product is recovered. m.p.=230° C.

NMR Spectrum (DMSO 250 MHz ppm):

equatorial OH
3.76 (s): OCH₃

4.13 approx.: 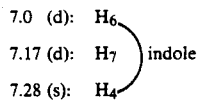 equatorial N 5.49 (dt, J=5-9 and 9): C H - axial OH 6.67 (dd, J=2 and 8.5): H₅  indole 7.25 (m):

0.63: 1H
1.2 to 3.2: the other protons

EXAMPLE 21

[(±) (14beta, 16alpha)]-14,15-dihydro-11-methoxy-20,21-dinoreburnamenin-14-ol (trans, dl)

The operation is carried out as in example 3 starting with 8 g of [(±) 16alpha]-11-methoxy-20,21-dinoreburnamenin-14(15H)-one and 7.91 g of crude product is obtained. m.p.=250° C. 1.5 g of this is triturated in 15 cm³ of 15N sodium hydroxide and 15 cm³ of methanol and taken to reflux for 3 hours. After cooling, the precipitate is separated, washed with methanol, then thoroughly with water. 11 g of expected product is obtained.

NMR Spectrum (DMSO 250 MHz ppm):

equatorial OH
3.75 (s): OCH₃

5.46 (dt, J=5.5 and 9): 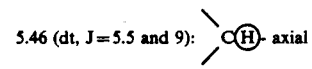 axial

NMR Spectrum (DMSO 250 MHz ppm):

6.47 (d, J=9): equatorial OH 6.66 (dd, J=2 and 8.5): H₅
7.21 (d, J=2): H₇  } indole
7.23 (d, J=8.5): H₄

1.05 to 3.02: the other protons

EXAMPLE 22

[(±) (14alpha, 16alpha)]-14,15-dihydro-11-methoxy-20,21-dinoreburnamenin-14-ol (trans, dl)

5 g of [(±) 14beta, 16alpha]-14,15-dihydro-11-methoxy-20,21-dinoreburnamenin-14-ol in 100 cm³ of N hydrochloric acid is agitated for 72 hours. The pH of the suspension is brought to 7 by the addition of 2N sodium hydroxide. The precipitate is separated, washed thoroughly with water, dried under reduced pressure at 70° C. and 4.4 g of crude product is obtained. After recrystallization from tetrahydrofuran 2.16 g of expected product is obtained. m.p.=245° C.

NMR Spectrum (DMSO 250 MHz ppm):

axial OH
3.77 (s): OCH₃

5.85 (m): 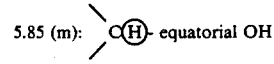 equatorial OH 6.18 (d, J=6.5): axial OH 6.64 (d, d, J=2 and 8.5): H₅
7.01 (d, J=2): H₇  } indole
7.21 (d, J=8.5): H₄

1.05 to 3.05: the other protons

EXAMPLE 23

Hemifumarate of (±) 11-methoxy-20,21-dinoreburnamenine (cis, dl)

The operation is carried out as in example 2 starting with 1.15 g of [(±) (14beta)]-14,15-dihydro-11-methoxy-20,21-dinoreburnamenin-14-ol. The solution is brought to dryness and the residue is taken up with methylene chloride, washed with 0.1N sodium hydroxide, then with water, and the organic phase is dried and brought to dryness. After chromatographing the residue on silica by eluting with an ethyl acetate-triethylamine mixture (95-5), 750 mg of product is obtained in the form of a base. m.p.=105° C. 1.208 g of base is dissolved in 40 cm³ of an isopropanol-ethyl acetate mixture (1-1) and 250 mg of fumaric acid is added, agitating for 16 hours at ambient temperature. After separating and washing with isopropanol and ethyl acetate, 1.107 g is obtained. m.p.=225° C.

NMR Spectrum (CDCl₃ 250 MHz ppm):

cis junction
3.86 (s): OCH₃

-continued

| NMR Spectrum (CDCl₃ 250 MHz ppm): |
|---|
|  4.51 (m): CH—N cis function |
| 5.29 (d,d J=6 and 7.5: ethylenic |
| 6.89 (d, J=7.5): ethylenic |
| 6.76 (d,d J=2 and 8.5): H₅ ⎫ |
| 6.84 (d, J=2): H₇ ⎬ indole |
| 7.34 (d, J=8.5): H₄ ⎭ |
| 0.90 (m): 1H |
| 1.45 to 3.40: the other protons |

EXAMPLE 24

Hemifumarate of [(±) 16alpha]-11-methoxy-20,21-norburnamenine (trans, dl)

The operation is carried out as in example 23 starting with 2.2 g of [(±) (14beta, 16alpha)]-14,15-dihydro-11-methoxy-20,21-dinoreburnamenin-14-ol, and after chromatography on silica, eluent: methylene chloride-ethyl acetate (1-1), 1.27 g of product is obtained in the form of a base. m.p.=128° C. The fumarate is prepared from 1.27 g of base and 1.23 g of expected product is obtained. m.p.=193° C.

NMR Spectrum (DMSO 250 MHz ppm):
3.78 (s): OCH₃
5.09 (dd, J=2 and 8): ethylene H in beta position of N
6.68 (dd, J=2 and 8): ethylene H in alpha position of N
7.19 (d, J=2): H₇ indole
7.25 to 7.35: H₅ and H₄ indole
6.61: ethylene H of the fumaric acid
1.2 to 3.15: the other protons

EXAMPLE 25

Neutral fumarate of [(±) (16alpha)]-14,15-dihydro-11-methoxy-20,21-dinoreburnamenine (trans, dl)

The operation is carried out as in example 12 starting with 2.23 g of [(±) (16alpha)]-11-methoxy-20,21-dinoreburnamenine and 220 mg of 10% palladium on carbon, and 2.2 g of oily product is obtained. This is triturated with isopropyl ether, separated, dried under reduced pressure at 50° C. and 1.17 g of product is obtained in the form of a base. m.p.=126° C. 740 mg of product is recovered from the mother-liquors. The neutral fumarate is prepared from 1.17 g of base dissolved in 20 cm³ of isopropanol and 30 cm³ of ethyl acetate. 1 g of expected product is obtained. m.p.=216° C.

NMR Spectrum (CDCl₃ 90 MHz) base:
3.88 ppm: OCH₃
6.72 to 6.83: H₅ and H₇ indole
7.31 to 7.42: H₄ indole
1.24 to 4.28: other protons

EXAMPLE 26

[(±) 14beta]-14,15-dihydro-10-methoxy-20,21-dinoreburnamenin-14-ol (cis, dl)

The operation is carried out as in example 3 starting with 8.7 g of (±) 10-methoxy-20,21-dinoreburnamenin-14(15H)-one and 5.73 g of crude product is obtained. It is recrystallized from tetrahydrofuran and 3.64 g of expected product is isolated. m.p.=225° C.

| NMR Spectrum: |
|---|
| equatorial OH |
| 3.75 (s): OCH₃ |
|  4.15 (m): —C(H)—N cis junction |
|  5.47 (dt, J=9-5.5-5.5): —C(H) axial OH |
| 6.32 (d, J=9): equatorial OH |
| 6.68 (dd, J=2.5 and 9): H₆ ⎫ |
| 6.88 (d, J=2.5): H₄ ⎬ indole |
| 7.54 (d J=9): H₇ ⎭ |

EXAMPLE 27

[(±) (14beta, 16alpha)]-14,15-dihydro-10-methoxy-20,21-dinoreburnamenin-14-ol (dl, trans)

The operation is carried out as in example 3 starting from 3.67 g of [(±) (16alpha)]-10-methoxy-20,21-dinoreburnamenin-14(15H)-one and 3.7 g of crude product is obtained. This is taken up with a chloroform-methanol mixture (2-1), filtered and then concentrated. A solution is prepared of the product obtained in 150 cm³ of tetrahydrofuran, and 50 cm³ of isopropyl ether is slowly added. 2.41 g of expected product is separated.

| NMR Spectrum (DMSO 250 MHz ppm): |
|---|
| 3.74 (s): OCH₃ |
|  5.43 (dt, J=5.5 and 9): —C(H) axial OH |
| 6.68 (dd, J=2 and 9): H₆ ⎫ |
| 6.87 (d, J=2): H₄ ⎬ indole |
| 7.53 (d, J=9): H₇ ⎭ |
| 1.1 to 3.05: the other protons |

EXAMPLE 28

[(±) (14alpha, 16alpha)]-14,15-dihydro-10-methoxy-20,21-dinoreburnamenin-14-ol (dl, trans)

4.8 g of [(±) (14beta, 16alpha)]-14,15-dihydro-10-methoxy-20,21-dinoreburnamenin-14-ol is put is suspension in 50 cm³ of 5N sodium hydroxide and 50 cm³ of methanol, and the whole is taken to reflux for 2 hours and 30 minutes. At ambient temperature, separation is carried out, followed by washing thoroughly with water until the pH of the wash water in neutral, and washing with 100 cm³ of methanol. 4.12 g of crude product is obtained which is taken to reflux for 15 hours under the same conditions as previously. The product recovered is taken up with a chloroform-methanol mixture (2-1), followed by filtering, concentrating and drying. 3.85 g of expected product is obtained.

| NMR Spectrum (DMSO 250 MHz ppm): | |
|---|---|
| axial OH | |
| 3.74 (s): OCH$_3$ | |
| 6.11 (d, J=7): OH | |
| 5.83: —C(H)— equatorial OH | |
| 7.31: (d, J=8.5) | H$_7$ ⎫ |
| 6.84: (d, J=2.5) | H$_4$ ⎬ indole |
| 6.68: (dd, J=2.5 and 8.5) | H$_6$ ⎭ |
| 1.05 to 3.05: the other protons | |

EXAMPLE 29

Hemifumarate of [(±) (16alpha)]-10-methoxy-20,21-dinoreburnamenine (trans, dl)

The operation is carried out as in example 2 starting with 1 g of [(±) (14beta, 16alpha)]-14,15-dihydro-10-methoxy-20,21-dinorebunamenin-14-ol. The solution obtained is filtered and brought to dryness under reduced pressure. The residue is triturated with a solution of sodium bicarbonate, followed by separating, washing thoroughly with water until the pH of the wash water is neutral, and drying under reduced pressure at 70° C. The residue is taken up with 20 cm³ of petroleum ether (b.p.=40°-70° C.). 820 mg of product is obtained in the form of a base. m.p.=145° C. The fumarate is prepared from 1.7 g of base dissolved in 50 cm³ of ethyl acetate. 1.55 g of expected product is obtained. m.p.=212° C.

| NMR Spectrum CDCl$_3$ 250 MHz (ppm): | |
|---|---|
| 3.85 (s): | OCH$_3$ |
| 5.04 (dd, J = 2 and 7.5): | ethylene H in beta position of N |
| 6.90 (dd, J = 3 and 7.5): | ethylene H in alpha position of N |
| 6.81 (dd, J = 2.5 and 8.5): | H$_6$ ⎫ |
| 6.94 (d, J = 2.5): | H$_4$ ⎬ indole |
| 7.21 (d, J = 8.5): | H$_7$ ⎭ |
| 1.3 to 3.2: the other protons | |

EXAMPLE 30

Hemifumarate of (±) 10-methoxy-20,21-dinoreburnamenine (cis, dl)

The operation is carried out as in example 6 starting with 2.02 g of [(±) (14beta)]-14,15-dihydro-10-methoxy-20,21-dinoreburnamenin-14-ol and 1.4 g of product is obtained in the form of a base. m.p.=134° C. The fumarate is prepared starting with 1.32 g of the latter and 1.14 g of expected product is isolated. m.p.=190° C.

| NMR Spectrum (CDCl$_3$ 250 MHz (ppm)): | |
|---|---|
| 3.86 (s): OCH$_3$ | |
| 4.54 (m): C(H)—N cis junction | |
| 6.89 (d, J=8): N—C(H)—C | |
| 5.27 (dd, J=6 and 8): —C(H)—CH | |

| NMR Spectrum (CDCl$_3$ 250 MHz (ppm)): | |
|---|---|
| 6.83 (dd, J=2.5 and 8.5): | H$_6$ ⎫ |
| 6.95 (d, J=2.5): | H$_4$ ⎬ indole |
| 7.21 (d, J=8.5): | H$_7$ ⎭ |
| 0.90 (m): 1H | |
| 1.45 to 3.40: other protons | |

By using the processes described above, the following examples were prepared:

EXAMPLE 31

[(±) (14alpha, 16alpha)]-9,11-dichloro-14,15-dihydro-20,21-dinoreburamenin-14-ol (trans, dl)

m.p.=260° C. Rf. 0.5 on alumina (methylene chloride-acetone 8-2).

EXAMPLE 32

[(±) (14beta, 16alpha)]-10,11-methoxy-14,15-dihydro-20,21-dinoreburnamenin-14-ol (trans, dl)

m.p.=252° C.

EXAMPLE 33

[(±) (14beta, 16alpha)]-9,10,11-trimethoxy-14,15-dihydro-20,21-dinoreburnamenin-14-ol (trans, dl)

m.p.=240° C.

EXAMPLE 34

[(±) (14beta, 16alpha)]-9-methoxy-14,15-dihydro-20,21-dinoreburnamenin-14-ol (trans, dl)

m.p.=233° C.

By carrying out a dehydration, as described above, on the alcohols obtained in examples 32, 33 and 34, the following products were prepared in the form of salts.

EXAMPLE 35

Acid maleate of [(±) (16alpha)]-10,11-dimethoxy-20,21-dinoreburnamenine (trans, dl)

m.p.=216° C. (salt). m.p.=208° C. (base).

EXAMPLE 36

Neutral fumarate of [(±) (16alpha)]-9,10,11-trimethoxy-20,21-dinoreburnamenine (trans, dl).

m.p.=211° C. (salt). m.p.=130° C. (base).

EXAMPLE 37

Acid maleate of [(±) (16alpha)]-9-methoxy-20,21-dinoreburnamenine (trans, dl)

m.p.=205° C. (salt). m.p.=146° C. (base).

EXAMPLE 38

[(±) (16alpha)]-11-nitro-14,15-dihydro-20,21-dinoreburnamenin-14-ol 2 g of sodium hydroboride is added is small fractions to a solution containing 2 g of [(±) (16alpha)-11-nitro-20,21-dinoreburnamenin-14(15H)-one and 100 cm³ of methanol. The mixture is heated to reflux for 50 minutes and 200 cm³ of iced water is added. The precipitate is separated, washed with water, dried at 75° C. under reduced pressure and 1.75 g of expected product is obtained.
m.p.>260° C.

| NMR Spectrum (DMSO 300 MHz ppm): |
| --- |
| 5.70 (m) 1/5 axial H ⎫ N— CH —OH |
| 6.05 (d) 4/5 H equatorial H ⎭ |
| 6.65 (d) equatorial ⎫ CH— OH |
| 6.93 (d) axial ⎭ |
| 7.53 (d) H₄ ⎫ |
| 7.93 (dd) H₅ ⎬ indole |
| 8.46 (d) H₇ ⎭ |
| 1.10 to 3.10: the other protons. |

EXAMPLE 39

[(±) (16alpha)]-11-nitro-20,21-dinoreburnamenine acid maleate 60 mg of copper trifluoromethane sulphonate is added to a suspension containing 1.25 g of product obtained in example 38 in 125 cm³ of xylene. The mixture is heated to reflux for 15 hours, filtered, and the solvent is eliminated under reduced pressure. The residue is chromatographed on silica (eluent: ethyl acetate) and 990 mg of product is obtained in the form of a base. m.p.=172° C. 1.24 g of base prepared as above is dissolved in 200 cm³ of an ethanol-ethyl acetate mixture (1-1), 487 mg of maleic acid dissolved hot in 50 cm³ of ethanol is added, with agitation for 2 hours at ambient temperature. The precipitate is separated, washed with ethanol and dried at 70° C. under reduced pressure. 1.44 g of expected product is recovered. m.p.>260° C.

| NMR Spectrum (CDCl₃ 250 MHz ppm): |
| --- |
| 5.27 (dd, J=2 and 8) HC⟍ Delta Z |
| ⟍CH |
| 7.00 (dd, J=3 and 8) |
| 7.47 (d, J=8.5) H₄ ⎫ |
| 8.00 (dd, J=2 and 8.5) H₅ ⎬ indole |
| 8.25 (d, J=2) H₇ ⎭ |
| 1.35 to 3.25: the CH and CH₂. |

EXAMPLE 40

[(±) (16alpha)]-9-nitro-14,15dihydro-20,21-dinoreburnamenin-14-ol

The operation is carried out as in example 38, using 2 g of [(±) (16alpha)]-9-nitro-20,21-dinoreburnamenin-14(15H)-one and 1.9 g of expected product is obtained. m.p.>260° C.

| NMR Spectrum (DMSO 250 MHz ppm): |
| --- |
| 5.71 (m) axial H N—(CH)—CH₂ |
| OH |
| 6.03 (d) equatorial H |
| 6.49 (d) axial OH |
| 6.75 (d) equatorial OH |
| 7.24 (t) H₆ ⎫ |
| 7.89 (dd) H₇ ⎬ indole |
| 8.10 (d) H₅ ⎭ |
| 1.15 to 3.2: the CH and CH₂ |

EXAMPLE 41

[(±) (16alpha)]-9-nitro-20,21-dinoreburnamenine acid maleate

The operation is carried out as in example 39 starting with 1.9 g of product obtained in example 40, 100 mg of copper trifluoromethane sulphonate and 200 cm³ of xylene. 1.65 g of product is obtained in the form of a base, m.p.=198° C. 1.57 g of base and 615 mg of maleic acid are used and 1.42 g of expected acid maleate is obtained. m.p.=228° C.

| NMR Spectrum (CDCl₃ 250 MHz ppm): |
| --- |
| from 1.36 to 3.41 (m): 12 H |
| 5.28 (dd, J = 12 and 8) ⎫ CH=CH |
| 6.99 (dd, J = 3 and 8) ⎭ |
| 7.19 (t, J = 8) H₆ ⎫ |
| 7.59 (dd, J = 8 and 1) H₇ ⎬ indole |
| 7.97 (dd, J = 8 and 1) H₅ ⎭ |

EXAMPLE 42

[(16alpha) (±)]-14,15-dihydro-11-dimethylamino-20,21-dinoreburnamenin-14-ol 1 g of sodium hydroboride is added in small fractions to a suspension containing 1.94 g of [(16alpha) (±)-11-dimethylamino-20,21-dinoreburnamenin-14(15H)-one prepared as in preparation 4 and 200 cm³ of methanol. The mixture is heated to reflux for 2 hours, cooled to ambient temperature, and a further 1 g of sodium hydroboride is added, with agitation for 2 hours at reflux. 500 cm³ of iced water is added, the precipitate is separated, washed with water, dried at 80° C. under reduced pressure and 1.64 g of expected product is obtained. m.p. approx. 260° C.

| NMR Spectrum (DMSO 300 MHz ppm): |
| --- |
| 5.41 (m, dd, J = 6 and 9) axial OH |
| 5.84 (d, s) equatorial OH |
| 6.37 (d) ⎫ OH |
| 6.09 (d) ⎭ |
| 6.62 (td) H₅ ⎫ |
| 6.79 (dd) H₇ ⎬ indole |
| 7.03 (d) H₇ ⎪ |
| 7.17 (d) H₄ ⎭ |

-continued

| NMR Spectrum (DMSO 300 MHz ppm): |
|---|
| 2.87 (s): the CH$_3$'s |
| from 1.1 to 3.1: the other protons. |

EXAMPLE 43

[(16alpha) (±)]-N,N-dimethyl-20,21-dinoreburnamenin-11-amine maleate 20 mg of para-toluenesulphonic acid is added to a suspension containing 400 mg of product prepared in example 42 in 40 cm$^3$ of toluene. The mixture is heated to reflux for 15 hours and concentrated to dryness. The residue is chromatographed on silica (eluent: ethyl acetate) and 290 mg of product is obtained in the form of a base. m.p.=132° C. 900 mg of base prepared as above is dissolved in 50 cm$^3$ of ethyl acetate and 10 cm$^3$ of ethanol. 712 mg of maleic acid in solution in 10 cm$^3$ of boiling ethanol is added. After maintaining for 3 hours under agitation at ambient temperature, the precipitate is separated, washed with ethanol and dried under reduced pressure at 70° C. 1 g of expected maleate is obtained. m.p.=228° C.

NMR Spectrum (CDCl$_3$ 250 MHz ppm):

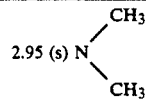

2.95 (s) N 5.01 (d,d J=2 and 7.5): N—CH=C (H)

6.94 (d,d, J=2 and 7.5): N—O (H)=CH 6.68 (s)  H$_7$
6.70 (d,d, J=7.5 and 2)  H$_5$  } indole
7.28 (d, J=7.5)  H$_4$

EXAMPLE 44

[(16alpha) (±)]-N-(14,15-dihydro-14-hydroxy-20,21-dinoreburnamenin-15-yl) acetamide 1.75 g of sodium hydroboride is added in small fractions to a suspension containing 1.75 g of [(16alpha) (±)]-N-(14,15-dihydro-14-oxo-20,21-dinoreburnamenin-11-yl) acetamide prepared as indicated in preparation 5 in 100 cm$^3$ of ethanol. The mixture is heated to reflux for 3 hours, cooled to ambient temperature, and 200 cm$^3$ of iced water is added. The precipitate is separate, washed with water, triturated in 50 cm$^3$ of methanol and dried at 80° C. under reduced pressure. 1.3 g of expected product is obtained. m.p.>260° C.

| NMR Spectrum (DMSO 300 MHz ppm): |
|---|
| 2.03: Ac |
| 5.99 (t): axial H N—CH—OH |
| 5.75: equatorial H |
| 6.00: mobile H |
| 7.09 to 7.25 H$_4$ and H$_5$ indole |
| 7.80 H$_7$ indole |
| 9.81: mobile H |
| 1.15 to 2.98: the other CH$_2$'s and CH |

EXAMPLE 45

[(16alpha) (±)]-N-20,21-dinoreburnamenin-11yl acetamide acid maleate 60 mg of para-toluenesulphonic acid is added to a suspension containing 1.2 g of product prepared in example 44 in 150 cm$^3$ of toluene and the mixture is heated to reflux for 16 hours; after cooling, filtering, and eliminating the solvent under reduced pressure, the residue is chromatographed on silica (eluent: methylene chloride-methanol (95-5)) and 1 g of product is obtained in the form of a base. m.p.=208° C. 1.2 g of product obtained as above is put in solution in 100 cm$^3$ of ethyl acetate and 453 mg of maleic acid, first dissolved in 50 cm$^3$ of ethyl acetate and 10 cm$^3$ of ethanol, is added. After agitation for 4 hours at ambient temperature, separating and drying at 50° C. under reduced pressure, 1.22 g of expected acid maleate is obtained. m.p.=217° C.

NMR Spectrum (CDCl$_3$ 300 MHz ppm):

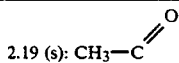

2.19 (s): CH$_3$—C 6.97 (dd, J=7.5 and 3): N—C (H)=CH 5.08 (dd, J=7.5 and 2): N—CH=C (H)

7.24: NH 7.96 (d, J=2)  H$_7$
7.34 (d, J=8)  H$_4$  } indole
6.88 (dd, J=2 and 8)  H$_5$ from 1.4 to 3.2: the other protons.

EXAMPLE 46

[(16alpha) (±)]-20,21-dinoreburnamenin-11-amine acid maleate 3 cm$^3$ of a 50% aqueous solution of potassium hydroxide is added to 1.5 g of base obtained in example 45 in solution in 100 cm$^3$ of ethanol. The mixture is heated to reflux for 24 hours and 200 cm$^3$ of water is added. The precipitate is separated and taken up in ethyl acetate. This organic phase is washed with water until neutral, and dried. The solvent is eliminated and the residue is chromatographed on silica (eluent: ethyl acetate-triethylamine 9-1). After drying at 65° C., 1 g of product is obtained in the form of a base. m.p.=252° C. 850 mg of this base is dissolved in a mixture of 100 cm$^3$ of ethyl acetate and 20 cm$^3$ of ethanol, 743 mg of maleic acid, first dissolved in 10 cm$^3$ of ethanol, is added, with agitation for 3 hours at ambient temperature. The precipitate is separated, washed with ethanol, and dried at 50° C. under reduced pressure. 1 g of expected product is recovered, m.p.=250° C., which is purified by trituration in an ethyl acetate-ethanol mixture (1-1).

NMR Spectrum (CDCl$_3$ 300 MHz ppm):

| 5.01 (dd, J = 7.5 and 2): | N—CH=C(H) |
| 6.84 (dd, J = 7.5 and 2): | N—O(H)=CH |
| 6.52 (dd, J = 8.5 and 2) | H$_5$ ⎫ |
| 6.64 (d, J = 2) | H$_7$ ⎬ indole |
| 7.22 (d, J = 8.5) | H$_4$ ⎭ |
| 3.50 (ep): | mobile 2H's |

-continued

| NMR Spectrum (CDCl₃ 300 MHz ppm): | |
|---|---|
| from 1.30 to 3.18: | the other protons. |

EXAMPLE 47

[(16alpha) (±)]-11-bromo-14,15-dihydro-20,21-dinoreburnamenin-14-ol 412 mg of sodium hydroboride is added in small fractions to a suspension containing 750 mg of (±) (16alpha)-11-bromo-20,21-dinoreburnamenin-14(15H)-one prepared as indicated in Belgian Patent No. 44087 B and 20 cm³ of methanol. 184 mg of lithium chloride is added, with agitation for 2 hours at ambient temperature and then for 30 minutes at 40° C. The reactive medium is poured over 100 cm³ of iced water, and the precipitate is separated, washed with water and dried under reduced pressure at 80° C. 711 mg of expected product is obtained. m.p.=245° C.

| NMR Spectrum (DMSO 400 MHz ppm): | |
|---|---|
| 5.52 (m, dd after exchange): | axial CH—OH |
| 5.88 (d, J = 6.5): | equatorial CH—OH |
| 6.61 (d, J = 8.5): | OH |
| 7.13 (dd, resolved) | $H_5$ ⎫ |
| 7.31 (d, resolved) | $H_4$ ⎬ indole |
| 7.83 (d, J = 1.5) | $H_7$ ⎭ |

EXAMPLE 48

[(±) (16alpha)]-11-bromo-20,21-dinoreburnamenine acid maleate 80 mg of para-toluenesulphonic acid is added to a suspension containing 1.5 g of product prepared as in example 47 in 100 cm³ of toluene and the whole is heated to reflux for 15 hours. After filtering and bringing to dryness, the residue is chromatographed on silica (eluent: ethyl acetate) and after drying at 50° C. under reduced pressure, 1.14 g of product is obtained in the form of a base. m.p.=133° C. 1.08 g of base is dissolved in 100 cm³ of ethyl acetate and 20 cm³ of ethanol, with agitation for 3 hours at ambient temperature. The precipitate is separated, washed with ethyl acetate and dried at 70° C. under reduced pressure. 1.33 g of expected acid maleate is recovered. m.p.=247° C.

| NMR Spectrum (CDCl₃ 400 MHz ppm): | |
|---|---|
| 5.12 (dd, J=7.5 and 2): CH | |
| 6.88 (dd, J=7.5 and 2): C(H)—N | |
| 7.18 (dd, J=8.5 and 2) | $H_5$ ⎫ |
| 7.30 (dd, J=8.5) | $H_4$ ⎬ indole |
| 7.45 (d, J=2) | $H_7$ ⎭ | other protons: 1.42 (m): 1H; 1.87 (m): 2H; 1.98 (m): 1H; 2.29 to 2.41 (m): 2H; 2.61 (m): 1H; 2.70 (m): 1H; 2.89 (dl): 1H; 2.97 to 3.08 (m): 2H; 3.14 (dd, J=11 and 5.5): 1H.

EXAMPLE 49

[(16alpha)]-14,15-dihydro-11-ethyl-20,21-dinoreburnamenin-14-ol 840 mg of sodium hydroboride, then 370 mg of lithium chloride, are added in small fractions to a suspension containing 1.3 g of [(16alpha) (±)]-11-ethyl-20,21-dinoreburnamenin-14(15H)-one prepared as indicated in preparation 6 and 100 cm³ of methanol. The mixture is heated to reflux for 6 hours and 300 cm³ of iced water is added. The precipitate formed is separated, washed with water, then dried at 100° C. under reduced pressure. The crude product is purified by trituration in methanol and 980 mg of expected product is recovered. m.p.=247° C.

| NMR Spectrum (DMSO 300 MHz ppm): | |
|---|---|
| 5.47 (m) axial: | N—C(H) —OH |
| 5.88: | equatorial N—C(H) —OH |
| 6.40 (d): | OH |
| 7.50 (d) | $H_7$ ⎫ |
| 7.25 (m) | $H_4$ and $H_7$ ⎬ indole |
| 6.88 (m) | $H_5$ ⎭ |
| 1.22 (m): | $CH_3$—$CH_2$ |
| 1.0 to 3.1 (m): | the other protons. |

EXAMPLE 50

[(±) (16alpha)]-11-ethyl-20,21-dinoreburnamenine acid maleate 50 mg of para-toluenesulphonic acid is added to 940 mg of product obtained in example 49 in suspension in 100 cm³ of toluene, then the whole is heated to reflux for one hour. The solution is concentrated to dryness, and the residue is chromatographed on silica (eluent: methylene chloride-methanol 97-3). 870 mg of expected product is obtained in the form of a base. m.p.=131° C. 770 mg of this base is dissolved in 50 cm³ of ethyl acetate and 20 cm³ of ethanol, and 320 mg of maleic acid, first dissolved in 10 cm³ of ethanol, is added. Agitation is carried out for 2 hours at ambient temperature, followed by separating and drying under reduced pressure at 60° C. 910 mg of expected maleate is recovered. m.p.=176° C.

| NMR Spectrum (CDCl₃ 300 MHz ppm): | |
|---|---|
| 1.28 (t): | C $H_3$ —$CH_2$ |
| 2.75 (q): | $CH_3$—C $H_2$ |
| 5.05 (d, J = 7.5 and 2): | N—CH=C H |
| 6.95 (m): | $H_5$ and other ethylene |
| 7.15 (s): | $H_7$ |
| 7.36 (d, J = 8): | $H_4$ |
| 1.41 (m) ⎫ | the other protons |
| 1.80 to 3.18 ⎭ | |

EXAMPLE 51

[(16alpha (±)]-14,15-dihydro-11-ethoxy-20,21-dinoreburnamenin-14-ol 160 mg of lithium borohydride is added in small fractions to a suspension containing 464 mg of [(16alpha) (±)]-11-ethoxy-20,21-dinoreburnamenin-14(15H)-one prepared as indicated in preparation 7 and 20 cm³ of methanol. After agitation for one hour at ambient temperature, 100 cm³ of water is added. The precipitate is separated, washed with water, dried at 70° C. under reduced pressure and 385 mg of expected product is obtained. m.p.=218° C.

NMR Spectrum (DMSO 400 MHz ppm):

1.34 (t) ⎫
4.00 (q) ⎭ OEt 5.43 (m, dd after exchange): axial C(H) —OH
5.83 (m, dd after exchange): equatorial C(H) —OH
6.44 (d, J = 8.5): CH—O(H)
7.21 (m): H₄ and H₇ of the indole
from 1.10 to 3.00 (m): the other protons.

EXAMPLE 52

[(16alpha) (±)]-11-ethoxy-20,21-dinoreburnamenine acid maleate 20 mg of para-toluenesulphonic acid is added to a suspension containing 350 mg of product obtained in example 51 and 20 cm³ of toluene. The solution is heated to reflux for 15 hours, filtered, and concentrated to dryness under reduced pressure. The residue is chromatographed on silica (eluent: ethyl acetate). 286 mg of product is obtained in the form of a base. m.p.=105° C. 260 mg of base is dissolved in 50 cm³ of ethyl acetate, 103 mg of maleic acid dissolved in 10 cm³ of ethyl acetate is added, with agitation for 3 hours at ambient temperature. After separation and drying at 70°C. under reduced pressure, 315 mg of expected product is recovered. m.p.=211° C.

NMR Spectrum (CDCl₃ 400 MHz ppm):

1.43 (t) ⎫
4.07 (q) ⎭ OEt 5.05 (dd, J=7.5 and 2)
6.89 (dd, J=7.5 and 3)

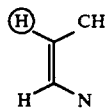

6.74 (dd, J=8 and 2) H₅ indole
6.84 (d, J=2) H₇ indole
1.3 to 3.15: the other protons.

EXAMPLE 53

[(16alpha) (±)]-14,15-dihydro-11-hydroxy-20,21-dinoreburnamenin-14-ol

The operation is carried out as in example 51 using 900 mg of [(16alpha) (±)]-11-hydroxy-20,21-dinoreburnamenin-14(15H)-one in 90 cm³ of toluene and 5.3 of diisobutylaluminium hydride in place of sodium hydroboride. 360 mg of expected producted is obtained (mixture of epimers). m.p.=240° C.

NMR Spectrum (DMSO 300 MHz ppm):

5.34 (dt, J = 6 and 9):  axial C(H) —OH (20%)
5.74 (d):                equatorial C(H) —OH (80%)
6.02 (d, J = 7) ⎫
6.26 (d, J = 9) ⎭ CH—O(H)
6.52 (dd) H₅ ⎫
6.79 (d) H₇  ⎪
7.07 (d) H₇  ⎬ indole
7.10 (d) H₄  ⎭

NMR Spectrum (DMSO 300 MHz ppm):
7.11 (d) H₄
8.83 (s):       mobile OH phenol
1.05 to 3.05 (m):   the other protons.

EXAMPLE 54

[(16alpha) (±)]-11-hydroxy-20,21-dinoreburnamenine

The operation is carried out as in example 52 starting with 360 mg of product obtained in example 53, using a few mg of copper trifluoromethane sulphonate in 20 cm³ of toluene. 250 mg of expected product is obtained. m.p.>260° C.

NMR Spectrum (DMSO 300 MHz ppm):
5.05 (dl, J=7): N—CH=C(H)
6.56 (dd, J=7 and 2): N—C(H)=CH
6.88 (sl) H₇ indole
7.17 (m) H₅ and H₄ indole
9.06 (s): OH
from 1.2 to 3.1 (m): the other protons.

EXAMPLE 55

(3alpha)-11-methyl-20,21-dinoreburnamenine maleate

Stage A: (3alpha) (−) 11-methyl-20,21-dinoreburnamenin-14(15H)-one 3.6 g of [(±)]-11-methyl-20,21-dinoreburnamenin-14(15H)-one (trans, dl) is dissolved hot in 50 cm³ of ethanol. 2.04 g of (−) di-O,O'-pivaloyl L-tartaric acid in solution in 22 cm³ of ethanol is added. After agitation for 2 minutes, the solution is maintained for 16 hours at ambient temperature. The crystallized product is separated, washed with ethanol and dried at 60° C. under reduced pressure. 4.67 g of crude product is obtained which is recrystallized from methanol. 2.17 g of intermediate salt is recovered [m.p.=260° C.; [alpha$_D$]=−137.5°±3.5° (c=0.5% dimethylformamide)] which is put in suspension in 50 cm³ of water and 50 cm³ of ethyl acetate. 5 cm³ of ammonia is added, with agitation for 30 minutes. The phases are separated, the organic phase is washed with water and dried, and the solvent is eliminated under reduced pressure. 1.38 g of expected 3alpha enantiomer is obtained. m.p.=198° C. [alpha$_D$]=−162.5°±3.5° (c=0.5% chloroform).

Stage B: (3alpha) 11-methyl-20,21-dinoreburnamenine 1.24 g of sodium hydroboride is added over 5 minutes to 1.53 g of product prepared as indicated in stage A in suspension in 30 cm³ of methanol with 10% water. The mixture is heated to reflux for 7 hours, then 30 cm³ of water and 1 cm³ of acetic acid are added. After agitation for 15 minutes at ambient temperature, 2 cm³ of ammonia is added, with further agitation for 15 minutes. The precipitate is separated, washed with water until neutral, and dried under reduced pressure at 60° C. 1.41 g of product is obtained (mixture of axial and equatorial OH) which is put in suspension in 28 cm³ of toluene. 70 mg of para-toluenesulphonic acid is added, heating for 16 hours at 100° C. A solution is obtained which is concentrated under reduced pressure. The residue is chromatographed on silica (eluent: methylene chloride-acetone 9-1) and 1.20 g of expected product is obtained. m.p.=134° C.

[alpha$_D$]=−433°±6° (c=0.5% chloroform).

Stage C: (3alpha) 11-methyl-20,21-dinoreburnamenine maleate 1.6 g of product prepared as in stage B is dissolved in 60 cm³ of ethyl acetate, 0.702 g of maleic acid in solution in 15 cm³ of ethyl acetate is added, with agitation for one hour at ambient temperature. The precipitate is separated and dried under reduced pressure at ambient temperature. 2.120 g of expected maleate is obtained. m.p.=195° C.

| Analysis: $C_{18}H_{20}N_2$, $C_4H_4O_4$: 380.448 | | | |
|---|---|---|---|
| Calculated: | C % 69.46 | H % 6.36 | N % 7.36 |
| Found: | 69.6 | 6.5 | 7.3 |

EXAMPLE 56

(16alpha) 11-methyl-20,21-dinoreburnamenine maleate

Stage A: [(16alpha) (±)]-11-methyl-20,21-dinoreburnamenin-14(15H)-one

The ethanol and methanol mother liquors obtained in example 55, stage A, are taken up during crystallization of the 3alpha enantiomer and concentrated to dryness. The residue is taken up with 250 cm³ of ethyl acetate and 150 cm³ of water, 10 cm³ of ammonia is added, with agitation for 30 minutes. The phases are separated; the organic phase is washed with water and concentrated under reduced pressure. 2.3 g of [(±) (16alpha)]-11-methyl-20,21-dinoreburnamenin-14(15H)-one is recovered, enriched with (16alpha) enantiomer. The synthesis is continued by operating as in stage A of example 55, using the 2.3 g of product prepared above and 1.3 g of (+) di-O,O'-pivaloyl D-tartaric acid. 1.93 g of intermediate salt is obtained [m.p.=260° C., [alpha$_D$]=+109.5°±3° (c=0.4% dimethylformamide)], then 1.22 g of expected product is obtained (16alpha enantiomer). m.p.=198° C.

[alpha$_D$]=+163.5°±3.5° (c=0.5% chloroform).

Stage B: (16alpha) 11-methyl-20,21-dinoreburnamenine

The operation is carried out as in stage B of example 55 starting with 1.53 g of product prepared as in stage A above. 1.17 g of reduced product is obtained (mixture of axial and equatorial OH) then 1.05 g of expected dehydrated product is obtained. m.p.=134° C.

[alpha$_D$]=+435.5°±6° (c=0.5% chloroform).

Stage C: (16alpha) 11-methyl-20,21-dinoreburnamenine maleate

The operation is carried out as in stage C of example 55 starting with 1.52 g of the product obtained in stage B above. 2 g of expected maleate is obtained. m.p.=195° C.

| Analysis: $C_{18}H_{20}N_2$, $C_4H_4O_4$: 380.448 | | | |
|---|---|---|---|
| Calculated: | C % 69.46 | H % 6.36 | N % 7.36 |
| Found: | 69.3 | 6.4 | 7.3 |

EXAMPLE 57

(3alpha) 11-methyl-20,21-dinoreburnamenine

The operation is carried out as in stage A of example 55 using at the start 3.2 g of [(±) (16alpha)]-11-methyl-20,21-dinoreburnamenine obtained in example 10 in 32 cm³ of ethyl acetate and 1.93 g of (−) di-O,O'-pivaloyl-L-tartaric acid in solution in 19 cm³ of acetone. 1.15 g of intermediate salt is obtained [m.p.=215° C., [alpha$_D$]=−340.5°±5.5° (c=0.5% dimethylformamide)], then 0.7 g of expected 3alpha enantiomer is obtained. m.p.=134° C.

[alpha$_D$]=−466.5°±6° (c=0.5% chloroform).

EXAMPLE 58

(16alpha) 11-methyl-20,21-dinoreburnamenine

The operation is carried out as in stage A of example 56 starting with the mother-liquors obtained during synthesis of the 3alpha enantiomer in example 57. 2.45 g of [(±) (16alpha)]-11-methyl-20,21-dinoreburnamenin-14(15H)-one is obtained, enriched with 16alpha enantiomer, then the synthesis is continued using 1.48 g of (+) di-O,O'-pivaloyl-D-tartaric acid. 1.33 g of intermediate salt is obtained [m.p.=215° C., [alpha$_D$]=305.5°±5° (c=0.5% dimethylformamide)], then 0.810 g of expected 16alpha enantiomer is obtained.

m.p.=134° C.

[alpha$_D$]=+447.5°±6° (c=0.5% chloroform).

EXAMPLE 59

(3alpha) 11-chloro-20,21-dinoreburnamenine

The operation is carried out as in stage A of example 55 using at the start 4.6 g of (±) 11-chloro-20,21-dinoreburnamenine prepared as in example 2 and 2.57 g of (−) di-O,O'-pivaloyl-L-tartaric acid in solution is 50 cm⁵ of ethyl acetate. 1.70 g of intermediate salt is obtained [m.p.=215° C., [alpha$_D$]−321°±5° (c=0.5% dimethylformamide)], then 1.06 g of expected 3alpha enantiomer is obtained.

m.p.=145° C.

[alpha$_D$]−441°±5° (c=1% chloroform).

The oxalate is prepared using oxalic acid. m.p. approx. 135° C.

| Analysis | | | | |
|---|---|---|---|---|
| Calculated: | C % 60.88 | H % 5.11 | N % 7.47 | Cl % 9.46 |
| Found | 60.7 | 5.2 | 7.2 | 9.4 |

EXAMPLE 60

(16alpha) 11-chloro-20,21-dinoreburnamenine

The operation is carried out as in stage A of example 56 starting with the mother-liquors obtained during synthesis of the 3alpha enantiomer of example 59. 3.5 g of (±) 11-chloro-20,21-dinoreburnamenine is obtained, enriched with 16alpha enantiomer, then synthesis is continued using 1.95 g of (+) di-O,O'-pivaloyl-D-tartaric acid. 1.82 g of intermediate salt is obtained [m.p. approx. 215° C., [alpha$_D$]=+323°±6° (c=0.5% dimethylformamide)], then 1.15 g of expected 16alpha enantiomer is obtained. m.p.=145° C.

[alpha$_D$]=+449°±5° (c=1% CHCl₃).

The oxalate was prepared using oxalic acid. m.p. #195° C.

| Analysis | | | | |
|---|---|---|---|---|
| Calculated: | C % 60.88 | H % 5.11 | N % 7.47 | Cl % 9.46 |
| Found | 60.7 | 5.1 | 7.4 | 9.5 |

PREPARATION 1

[(±) 16alpha]-11-chloro-20,21-dinoreburnamenin-14(15H)-one (trans dl) used at the start of example 1

Stage A:
1-[2-(6-chloro)-1H-indol-3-yl)ethyl]-2-piperidinone 22.37 g of 6-chloro tryptamine and 9.21 g of potassium carbonate are taken to reflux in 200 cm$^3$ of ethoxy ethanol and 21 cm$^3$ of ethyl bromovalerate in 42 cm$^3$ of ethoxy ethanol is introduced over 3 hours 30 minutes, maintaining reflux for another hour. After cooling, the precipitate is separated, washed with methanol and the filtrate is concentrated to dryness. The residue is triturated in 50 cm$^3$ of 2N hydrochloric acid, then in 150 cm$^3$ of water. The solid product obtained is washed thoroughly with water until the pH of the wash water is neutral. It is taken up in methylene chloride, the organic solution is dried and brought to dryness, and the residue is triturated in 200 cm$^3$ of isopropyl ether. 25.5 g of expected product is obtained. m.p.=191° C.

Stage B: 2,3,4,6,7,12-hexahydro-10-chloro indolo[2,3-a]quinolizine 2 g of product obtained above in 10 cm$^3$ of dioxan is taken to 60° C. and 2 cm$^3$ of phosphoric oxychloride is slowly added, then agitation is maintained under these conditions for another hour. The suspension is poured slowly into a solution at 0° C. made up of 4 cm$^3$ of concentrated perchloric acid in 50 cm$^3$ of water and maintained under agitation at 0° C. for another hour. The perchlorate obtained is dissolved, while still humid, in 10 cm$^3$ of acetone at 40° C. under inert atmosphere and shaded from the light. 20 cm$^3$ of concentrated ammonia is introduced over 10 minutes at 40° C., with agitation for 15 minutes at 40° C. 10 cm$^3$ of water is added, and the whole is cooled to 0° C. for 30 minutes. The precipitate is separated, washed thoroughly with water and dried under reduced pressure at 50° C., and 1.54 g of expected product is obtained. m.p.=165° C.

Stage C: [(±) 16alpha]-11-chloro-20,21-dinoreburnamenin-14(15H)-one (trans dl) used at the start of example 1.

1.38 g of 2,3,4,6,7,12-hexahydro-10-chloro indolo[2,3-a]quinolizine is dissolved in 5 cm$^3$ of dimethylformamide, 0.8 cm$^3$ of ethyl iodoacetate is added, and the mixture is agitated for 6 hours at ambient temperature. 5 cm$^3$ of hydriodic acid in 5 cm$^3$ of water is added with precaution and the whole is taken to reflux for 10 hours. After cooling to ambient temperature, 20 cm$^3$ of water and ice is added to the suspension obtained, with agitation for one hour at 0° C. After separating and washing with water, the product is put in 25 cm$^3$ of a tetrahydrofuran-methanol mixture (6-4), cooled to 0° C., and sodium borohydride is added in small fractions, agitating at 0° C. for another hour. 1.5 cm$^3$ of acetic acid is added slowly, with agitation for 10 minutes, followed by alkalizing by the addition of 3 cm$^3$ of concentrated ammonia. 50 cm$^3$ of water is added and extraction is carried out with methylene chloride. The organic phase is washed with water, dried and concentrated to dryness, and the residue is chromatographed on silica (eluent: methylene chloride-methanol 95-5).

500 mg of expected product is isolated. m.p.=205° C.

Using the same process, starting with corresponding substituted tryptamines, the following products were prepared:

[(±) (16alpha)]-11-methyl-20,21-dinoreburnamenin-14(15H)-one (trans, dl) used at the start of example 7.

[(±) (16alpha)]-10-methyl-20,21-dinorburnamenin-14(15H)-one (trans, dl) used in example 13.

[(±) (16alpha)]-11-methoxy-20,21-dinoreburnamenin-14(15H)-one (trans, dl) used at the start of example 21.

[(±) (16alpha)]-10-methoxy-20,21-dinoreburnamenin-14(15H)-one (trans, dl) used at the start of example 27.

[(±) (16alpha)]-10-cloro-20,21-dinoreburnamenin-14(15H)-one (trans, dl) used at the start of example 4.

PREPARATION 2

(±) 10-chloro-20,21-dinoreburnamenin-14(15H)-one (cis, dl) used at the start of example 3

Stage A:
1-[2-(5-chloro-1H-indol-3-yl)ethyl]-2-piperidinone

The operation is carried out as in Stage A of preparation 1 starting with 57.6 g of 5-chloro tryptamine and 31.5 g of expected product is obtained. m.p.=152° C.

Stage B: 9-chloro-2,3,4,6,7,12-hexahydro indolo[2,3-a]quinolizine 26.7 g of product obtained previously is dissolved in 30 cm$^3$ of dimethylaniline and 150 cm$^3$ of dioxan, operating as in stage B of preparation 1. 22.2 g of expected product is obtained, m.p.=150° C., which is used quickly for the following stage.

Stage C: Ethyl 9-chloro-1,2,3,4,6,7,12,12 b octahydro indolo[2,3-a]quinolizine-2-acetate (cis dl)

Under inert atmosphere and shaded from the light, 100 cm$^3$ of dimethylformamide is heated to 60° C., 15.64 g of sodium iodide is added and the mixture is allowed to return slowly to 55° C. 11.6 cm$^3$ of ethyl bromo acetate is added, the mixture is maintained under agitation at 60° C. for 1 hour 30 minutes and allowed to return slowly to ambient temperature. Hydroquinone is added, then 18 g of product obtained in the beta position, and the whole is left under agitation for 72 hours. It is poured over 55 cm$^3$ of perchloric acid in one liter of iced water, with agitation for one hour at 0° C., separating, washing with iced water, and drying under reduced pressure. The perchlorate obtained is dissolved in 300 cm$^3$ of a tetrahydrofuran-methanol mixture (1-1) at less than 20° C., 4 g of sodium hydroboride is added in small fractions, and agitation is carried out for 2 hours. 20 cm$^3$ of acetic acid is added, with agitation for a quarter of an hour, and 40 cm$^3$ of ammonia is introduced, followed by 500 cm$^3$ of water. This suspension is extracted with ethyl acetate, the organic phase is dried and concentrated to dryness, and the residue is chromatographed on silica (eluent: ethyl acetate-methylene chloride (1-1)). 9.95 g of expected product is recovered. m.p. 165° C.

Stage D: (±) 10-chloro-20,21-dinoreburnamenin-14(15H)-one (cis dl) used at the start of example 3

1.8 g of sodium methylate is added in small fractions to a solution containing 7.65 g of product obtained in C in 50 cm$^3$ of methanol and the mixture is taken to reflux for 45 minutes.

At ambient temperature, the suspension obtained is poured over 50 cm³ of water. The precipitate is separated, washed with water until the pH of the wash water is 7, dried under reduced pressure at 100° C. and 5.87 g of expected product is obtained. m.p.=214° C.

Proceeding in the same manner, starting with corresponding substituted tryptamines, the following products were prepared:

(±) 11-methyl-20,21-dinoreburnamenin-14(15H)-one (cis, dl) used in example 9.
(±) 10-methyl-20,21-dinoreburnamenin-14(15H)-one (cis, dl) used in example 14.
(±) 11-methyl-20,21-dinoreburnamenin-14(15H)-one (cis, dl) used in example 20.
(±) 10-methoxy-20,21-dinoreburnamenin-14(15H)-one (cis, dl) used in example 26.

PREPARATION 3

[(±) (16alpha)]-11-nitro-20,21-dinoreburnamenin-14(15H)-one and [(±) (16alpha)]-9-nitro-20,21-dinoreburnamenin-14(15H)-one used at the start of examples 38 and 40

A solution of 20 g of (3beta, 16alpha) (±) 20,21-dinoreburnamenin-14(15H)-one in 100 cm³ of acetic acid is added to a mixture containing 30 cm³ of nitric acid and 30 cm³ of acetic acid, maintaining the temperature between 30° C. and 35° C., with agitation for one hour. 3 operating units are then prepared, put together and poured into 2 liters of iced water. Alkalizing is carried out by the addition of concentrated ammonia; the precipitate formed is separated, washed with water, dried at 60° C. under reduced pressure and chromatographed on silica (eluent: ethyl acetate). 41.8 g of 11-nitro isomer is obtained (m.p.=196° C.) and 15.7 g of 9-nitro isomer is obtained (m.p.=174° C.).

| NMR Spectrum (CDCl₃ 250 MHz ppm): | | |
|---|---|---|
| 11-nitro isomer | | |
| 1.29 (m): | 1H | |
| 1.76 to 2.14 (m): | 4H | |
| 2.32 to 3.24 (m): | 9H | |
| 7.43 (d, J = 8.5) | H₄ | ⎫ |
| 8.14 (dd, J = 8.5 and 2) | H₅ | ⎬ indole |
| 9.13 (d, J = 2) | H₇ | ⎭ |
| 9-nitro isomer | | |
| 1.29 (m): | 1H | |
| 1.83 to 3.29 (m) approx. | 13H | |
| 7.35 (t, J = 8) | H₆ | ⎫ |
| 8.03 (dd, J = 8 and 1) | H₇ | ⎬ indole |
| 8.75 (dd, J = 8 and 1) | H₅ | ⎭ |

PREPARATION 4

[(16alpha) (±)]-11-dimethylamino-20,21-dinoreburnamenin-14(15H)-one Used at the Start of Example 42

Stage A: [(16alpha) (±)]-11-amino-20,21-dinoreburnamenin-14(15H)-one 22.1 g of [(16alpha) (±)]-11-nitro-20,21-dinoreburnamenin-14(15H)-one prepared as indicated in preparation 3 is hydrogenated for 15 hours under 500 g of pressure in a mixture containing 750 cm³ of ethyl acetate and 750 cm³ of ethanol in the presence of 900 mg of platinum oxide. After filtering, the organic phase is concentrated to dryness, the residue is triturated in isopropyl ether, dried at 50° C. under reduced pressure and 18.2 g of expected product is obtained. m.p.=172° C. then 210° C.

| NMR Spectrum (CDCl₃ 250 MHz ppm): | |
|---|---|
| 1.21 (m) | 1H |
| 1.75 to 2.03 (m) | 4H |
| 2.25 to 3.15 (m) | 9H |
| 3.73 (m) | NH₂ |
| 6.65 (dd, J=8 and 2) | H₅ |
| 7.16 (d, J=8) | H₄  indole |
| 7.75 (d, J=2) | H₇ |

Stage B: [(16alpha) (±)]-11-dimethylamino-20,21-dinoreburnamenin-14(15H)-one 2 g of product prepared above in solution in a mixture containing 50 cm³ of acetonitrile and formic aldehyde is agitated for 10 minutes under inert atmosphere. 1.33 g of sodium cyano borohydride is added, with agitation for 30 minutes at ambient temperature. 0.7 cm³ of acetic acid is added drop by drop and agitation is continued for 15 hours. 100 cm³ of water is added, alkalizing by the addition of concentrated ammonia. Extraction is carried out with ethyl acetate; the extracts are washed with water, dried and concentrated to dryness under reduced pressure. After chromatography on silica (eluent: ethyl acetate), 1.94 g of pure product is obtained. m.p.=164° C.

| NMR Spectrum (DMSO 250 MHz ppm): | | |
|---|---|---|
| 2.99 (s) | the N—CH₃'s | 1) |
| 6.76 (dd) | H₅ | |
| 7.24 (d) | H₄ | indole |
| 7.82 (d) | H₇ | |
| 1.24 (m) | 1H | the other |
| 1.7 to 3.2 (m) | | protons0509322715202 |

PREPARATION 5

[(16alpha) (±)]-N-(14,15-dihydro-14-oxo-20,21-dinoreburnamenin-11-yl) acetamide Used at the Start of Example 44

1.5 cm³ of triethylamine is added to 1.5 g of [(16alpha) (±)]-11-amino-20,21-dinoreburnamenin-14(15H)-one prepared as indicated in stage A of preparation 4 in solution in 30 cm³ of tetrahydrofuran. 0.4 cm³ of acetyl chloride is added drop by drop, with agitation for 30 minutes at ambient temperature. 100 cm³ of water is added, the precipitate is separated, washed with water and dried at 100° C. under reduced pressure. 1.75 g of expected product is obtained. m.p.>260° C.

NMR Spectrum (CDCl₃ 250 MHz ppm):

2.18 (s): CH₃—C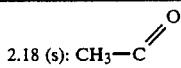

1.25 (m): 1H
1.8 to 3.2 (m): the other protons 7.29 (d, J=8.5)   H₄ ⎫
7.72 (dd, J=8.5 and 2)  H₅ ⎬ indole
8.12 (d, J=2)    H₇ ⎭

-continued

NMR Spectrum (CDCl₃ 250 MHz ppm):

7.64 (s): NH—C 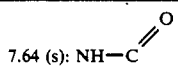

PREPARATION 6

[(16alpha) (±)]-11-ethyl-20,21-dinoreburnamenin-14(15H)-one

Stage A: [(16alpha) (±)]-11-ethenyl-20,21-dinoreburnamenin-14(15H)-one 2.9 cm³ of vinyltributyltin, then 100 mg of tetrakis-(triphenyl phosphine)-palladium are added to a solution containing 3 g of [(16alpha) (±)]-11-bromo-20,21-dinoreburnamenin-14(15H)-one and heated to reflux for 24 hours. After filtering, the filtrate is concentrated under reduced pressure, the residue is taken up in ethyl acetate and filtered, and the solvent is eliminated under reduced pressure. After chromatography on silica (eluent: ethyl acetate), 2.1 g of expected product is obtained. m.p.=164° C.

NMR Spectrum (CDCl₃ 300 MHz ppm):

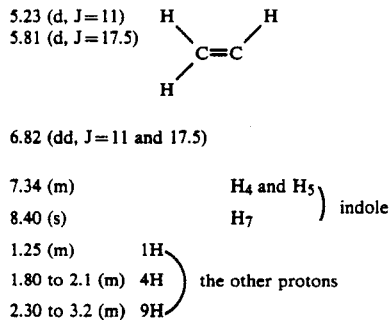

| 5.23 (d, J=11) | | |
| 5.81 (d, J=17.5) | | |
| 6.82 (dd, J=11 and 17.5) | | |
| 7.34 (m) | H₄ and H₅ | indole |
| 8.40 (s) | H₇ | |
| 1.25 (m) | 1H | |
| 1.80 to 2.1 (m) | 4H | the other protons |
| 2.30 to 3.2 (m) | 9H | |

Stage B: [(16alpha) (±)]-11-ethyl-20,21-dinoreburnamenin-14(15H)-one 100 mg of platinum hydroxide is added to 2 g of product prepared in stage A in solution in 100 cm³ of ethanol and hydrogen under 500 g of pressure for 6 hours. After filtering, 0.6 cm³ of concentrated hydrochloric acid is added to the ethanol solution. After agitation for 30 minutes, the hydrochlorate is separated and taken up in 200 cm³ of water, alkalizing by the addition of concentrated ammonia. The precipitate is separated, washed with water, dried and 1.35 g of expected product is recovered. m.p.=130° C.

NMR Spectrum (CDCl₃ 300 MHz ppm):

| 1.28 (t) | CH₃—CH₂ | |
| 2.76 (p) | CH₃—CH₂ | |
| 7.12 (dd) | H₅ | |
| 7.32 (d) | H₄ | indole |
| 8.21 (d) | H₇ | |
| 1.2 | 1H | the other protons |
| 1.8 to 3.15 (m) | | |

PREPARATION 7

[(16alpha) (±)]-11-ethoxy-20,21-dinoreburnamenin-14(15H)-one

Stage A: [(16alpha) (±)]-11-hydroxy-20,21-dinoreburnamenin-14(15H)-one

The operation is carried out according to the method described in Pub. Bull. Soc. Chim. Belg 88 No. 1-2 (1979) p. 93, using at the start 560 mg of [(16alpha) (±)]-11-amino-20,21-dinoreburnamenin-14(15H)-one, 180 mg of sodium nitrite in 2 cm³ of water in the presence of 4 cm³ of 35% sulphuric acid, then 7.5 g of trihydrated cupric nitrate and 290 mg of copper oxide. 220 mg of expected product is obtained.

Stage B: [(16alpha) (±)]-11-ethoxy-20,21-dinoreburnamenin-14(15H)-one 136 mg of sodium hydride is added to a solution containing 800 mg of product prepared as in stage A and 10 cm³ of dimethylformamide, under inert atmosphere, with agitation for 30 minutes. 0.25 cm³ of ethyl iodide is added, leaving in contact for one hour. 200 cm³ of water is added, and extraction is done with ethyl acetate. The organic phase is washed with water, dried and concentrated to dryness. The residue is chromatographed on silica (eluent: ethyl acetate) and 464 mg of expected product is obtained. m.p.=148° C.

NMR Spectrum (CDCl₃ 250 MHz ppm):

| 1.43 (t) | OCH₂—CH₃ | |
| 4.10 (q) | | |
| 6.88 (dd, J=8.5 and 2) | H₅ | |
| 7.27 (d, J=8.5) | H₄ | indole |
| 7.94 (d, J=2) | H₇ | |
| 1.26 (m) | 1H | the other protons |
| 1.8 to 3.2 (m) | | |

PREPARATION 8

[(16alpha) (±)]-11-chloro-20,21-dinoreburnamenin-14(15H)-one 6.9 g of [(16alpha) (±)]-11-amino-20,21-dinoreburnamenin-14(15H)-one in solution in 100 cm³ of 6N hydrochloric acid is cooled to −5° C., then a solution of sodium nitrite in 3 cm³ of water is added drop by drop. After agitation for 20 minutes at −5° C., the mixture is poured into a solution of cuprous chloride in 50 cm³ of 6N hydrochloric acid. After agitation for 30 minutes at 90° C., 500 cm³ of iced water is added, alkalizing with concentrated ammonia. The precipitate is separated, washed with water, dried at 70° C., chromatographed on silica (eluent: methylene chloride-methanol 96-4) and 6.2 g of expected product is obtained. m.p.=205° C.

EXAMPLE 61

Pharmaceutical Composition

Tablets were prepared corresponding to the following formula:

| Product of example 2 | 300 mg |
|---|---|
| Excipient q.s. for a tablet | 350 mg |

(detail of excipient: talc, magnesium stearate, aerosil).

EXAMPLE 62

Pharmaceutical Composition

Tablets were prepared corresponding to the following formula:

| Product of example 10 | 300 mg |
|---|---|
| Excipient q.s. for a tablet | 350 mg |

(detail of excipient: talc, magnesium stearate, aerosil).
The same with the product of example 10.

PHARMACOLOGICAL STUDY

1) Affinity for adrenergic alpha2 receptors:

10 cortices removed from the brains of male rats weighing on average 150 g are homogenized in 90 ml of 0.32M sucrose. After centrifuging 1,000 g of the homogenized mixture for 10 minutes at 0° C., the supernatant is centrifuged at 30,000 g for 10 minutes at 0°/+4° C. The deposit is put in suspension in 240 ml of buffer TrisHCl 50 mM pH 7.7, and centrifuged at 30,000 g for 15 minutes at 0°/+4° C. The new deposit obtained is put in suspension in 480 ml of buffer $NaKPO_4$ pH 7.4 50 mM.

2 ml of suspension is then incubated for 45 minutes at 25° C. in the presence of $^3H$ rauwolscine at a 0.15 nM concentration:

i) alone,
ii) with increasing concentrations of the product under test or,
iii) in order to determine the non-specific fixation, with non-radioactive phentolamine at a $10^{-5}M$ concentration.

The incubated suspensions are filtered on Whatman GF/C and the filters are washed three times with 5 ml of buffer $NaKPO_4$ pH 7.4 at 0° C. The radioactivity of the filters is measured by liquid scintillation.

The affinity of the product tested for adrenergic alpha2 receptors is given in relation to the phentolamine as a reference product.

CD = concentration of phentolamine inhibiting 50% of the specific fixation of $^3H$ rauwolscine;
CX = concentration of the product under test inhibiting 50% of the specific fixation of $^3H$ rauwolscine.

The relative affinity is given by the relation:

$$RAL = 100 \frac{CD}{CX}$$

Results:

| Products of examples | RAL |
|---|---|
| 2 | 110 |
| 4 | 35 |
| 5 | 55 |
| 10 | 160 |
| 12 | 39 |
| 16 | 136 |
| 18 | 39 |

2) Asphyxic anoxemia:

The test is carried out using a Sprague Dawley (Charles River) male rat anaesthetized with ethyl ether, immobilized (tube curare 1 mg/kg I.V.) and artificially ventilated with air. The electrocorticogram (ECoG) and the arterial pressure are recorded. The rectal temperature is maintained at around 36° C. and the level of carbon dioxide in the blood is maintained between 35 and 40 torr. The products are administered at a dose of 10 mg/kg by intravenous route in a volume of 1 ml/kg 3 minutes before asphyxia obtained by stopping the artificial respiration. The latency time for the disappearance of the ECoG is measured.

Results:

| Product of example | % of variation of the latency time for disappearance of the ECoG after asphyxia |
|---|---|
| 2 | +43 |
| 5 | +26 |
| 8 | +37 |
| 10 | +47 |
| 12 | +18 |
| 16 | +22 |
| 21 | +30 |
| 22 | +18 |
| 24 | +35 |
| 25 | +20 |
| 28 | +35 |
| 29 | +25 |

3) Test for hypobar anoxemia in a mouse

This consists of measuring for a maximum duration of 3 minutes the survival time of mice placed in a 2 liter chamber in which a 600 mmHg depression is carried out. Mice deprived of food for 6 hours are used. The products are administered at a dose of 10 mg/kg by intraperitoneal route in a volume of 0.2 ml/10 g 60 minutes before the test.

The increase in survival time is noted, expressed as a percentage of the animals treated in relation to the control animals, submitted to the same conditions.

The following results were obtained:

| Product of example | % of increase in survival time |
|---|---|
| 39 | 14 |
| 40 | 22 |
| 41 | 13 |

Anti-Amnesic Effect in a Passive Avoidance

Rats are placed individually in the lighted compartment of a box having two compartments, the other one being dark. They take refuge immediately in the dark compartment and upon their entry the rats receive an electric shock (1 mA/5 sec) from the grated floor. The animals are then divided into 3 groups: the first group (control) does not undergo any other manipulation. In the second group, the electric shock is immediately followed by the application of an amnesic electric shock treatment (60 mA, 0.6 ms, 0.6 s) (electric shock treatment control group). The third group is identical to the second, but the electric shock treatment is immediately followed by the administration of the compound under test (treated group). Twenty-four hours later, the animals are replaced in the lighted compartment of the box and the latency time of entry into the dark compartment is measured (up to 300 sec. maximum). For the controls, this time is close to 300 sec. The electric shock treatment controls on the other hand move into the dark compartment much more rapidly (amnesic effect). The products with anti-amnesic effect increase the latency of entry and aim to bring it back to a value comparable to that of the controls without electric shock treatment.

In this test the compound of example 10 reverses the anti-amnesic effect of an electric shock treatment at a dose of 2 mg/kg by oral route.

4) Test for spontaneous alternation after septal cholinergic injury

The behaviour of spontaneous alternation is an essential characteristic of the behavioural performance of the rat, which, put in a situation of choice between a familiar stimulus and a new stimulus, will choose the latter. Thus, in the case of a labyrinth Y, the animal will preferably choose an arm which has not yet been explored as opposed to an arm that he has just visited (spontaneous alternation). This faculty of discrimination between the "familiar" and the "new" implies the coming into play of a form of memory, the Short Term Memory or Work Memory. The performances of spontaneous alternation allow therefore an evaluation of the capacity of this type of memory.

The method used consists of creating a mnesic deficit in the rat, by lesion of the septo-hippocampic cholinergic system, and of researching whether the product under test is capable of reversing this deficit. In the present case, this deficit is evaluated in a spontaneous alternation behaviour; the lesioned animal has alternation performances of about 50%, because it carries out its choices by chance.

Each experiment comprises a control-vehicle group, a lesioned-vehicle group and one or two lesioned groups receiving the product under test. For four days, each rat is submitted to one session per day, containing four tests which are each divided into two parts: a forced choice and a free choice. The product is administered by intra-peritoneal (i.p.) route 30 minutes before each session.

The product of example 10 reverses the mnesic deficit caused by the septal cholinergic lesion in a range of doses from 1 to 10 mg/kg i.p..

5) Test for anti-depressive activity

The tests are carried out on groups of 5 Sprague Dawley rats. The unaffected animals are placed for 15 minutes in a vertical cylinder of plexiglass (diameter: 18 cm, height: 40 cm) containing water at 25° C. at a height of 15 cm (initial swimming test). They are then dried for 15 minutes in a chamber heated to 32° C.; 24 hours later, they are replaced in the cylinder, filled with water, and the total duration of the periods of immobility is measured over 5 minutes.

The compound is administered i.p. successively 24, 5 and half an hour before the test. The first administration takes place immediately after the initial swimming test, just before the animals are replaced in their breeding box.

The averages of the treated groups are compared with those of the control group using Dunnett's test.
Results:

| Product of example | AD$_{50}$ mg/kg |
|---|---|
| 10 | 13 |

We claim:

1. A compound selected from the group consisting of a compound of the formula

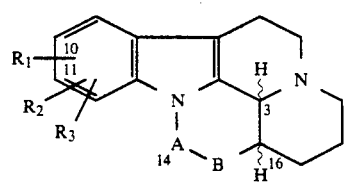

in which $R_3$ and $R_2$ are hydrogen and $R_1$ is selected from the group consisting of halogen, alkyl or alkoxy of 1 to 5 carbon atoms, hydroxy, trifluoromethyl, nitro, amino, alkylamino or dialkylamino in which the alkyl has from 1 to 5 carbon atoms, an acylamino in which the acyl is remainder of an aliphatic acid of 1 to 6 carbon atoms, and in which the group: is

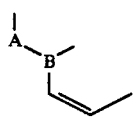

the said products of formula I being in all the possible racemic or opticaly active isomer forms and their non-toxic, pharmaceutically acceptable acid addition salts.

2. Compounds of claim 1, characterized in that $R_1$ is selected from the group consisting of methyl, ethyl, methoxy, ethoxy, chlorine, hydroxy, trifluoromethyl or nitro.

3. Compounds of claim 1 characterized in that $R_1$ is in position 10 or 11 and is methyl, ethyl, methoxy or ethoxy, chlorine, hydroxy, trifluoromethyl or nitro.

4. Compounds of claim 1 characterized in that $R_1$ is in position 9, 10, or 11, and is chlorine atom, methyl, ethyl, methoxy or ethoxy.

5. Compounds of claim 1 characterized in that the hydrogen atom in position 3 and the hydrogen atom in position 16 are trans.

6. A compound of claim 1 selected from the group consisting of

[(±) (16-alpha)]-11-chloro-20,21-dinoreburnamenine,
[(±) (16-alpha)]-11-methoxy-20,21-dinoreburnamenine and
[(±) (16-alpha)]-11-methyl-20,21-dinoreburnamenine.

7. A composition for treating cerebral insufficiencies of an anoxic or isochemic origin comprising an amount of at least one compound of claim 1 sufficient to treat said cerebral insufficiencies and an inert pharmaceutical carrier.

8. The composition of claim 7 wherein $R_1$ is individually selected from the group consisting of hydrogen, methyl, ethyl, methoxy, ethoxy, chlorine, hydroxy, trifluoromethyl and nitro.

9. The composition of claim 7 wherein $R_1$ is selected from the group consisting of methyl, ethyl, methoxy, ethoxy, chlorine, hydroxy, trifluoromethyl and nitro in the 10- or 11-position.

10. The composition of claim 7 wherein the active compound is one compound selected from the group consisting of

[(±) (16-alpha)]-11-chloro-20,21-dinoreburnamenine,
[(±) (16-alpha)]-11-methoxy-20,21-dinoreburnamenine and

[(±) (16-alpha)]-11-methyl-20,21-dinoreburnamenine.

11. A method of treating cerebral insufficiencies of anoxic or isochemic origin in warm blooded animals comprising administering to warm blooded animals a sufficient amount of at least one compound of claim 1 to treat cerebral insufficiencies in anoxic or isochemic origin.

12. The method of claim 11 wherein $R_1$ is individually selected from a group consisting of hydrogen, methyl, ethyl, methoxy, ethoxy, chlorine, hydroxy, trifluoromethyl and nitro.

13. The method of claim 11 wherein $R_1$ is selected from the group consisting of methyl, ethyl, methoxy, ethoxy, chlorine, hydroxy, trifluoromethyl and nitro in the 10- or 11-position.

14. The method of claim 11 wherein the active compound is one compound selected from the group consisting of

[(±) (16-alpha)]-11-chloro-20,21-dinoreburnamenine,
[(±) (16-alpha)]-11-methoxy-20,21-dinoreburnamenine and
[(±) (16-alpha)]-11-methyl-20,21-dinoreburnamenine.

* * * * *

UNITED STATES PATENT AND TRADEMARK OFFICE
CERTIFICATE OF CORRECTION

PATENT NO. : 5,093,337
DATED : Mar. 3, 1992
INVENTOR(S) : NURGUN AKTOGU; FRANCOIS CLEMENCE and CLAUDE OBERLANDER It is certified that error appears in the above-identified patent and that said Letters Patent is hereby corrected as shown below:

Col. Line
42   19 & 20    " is 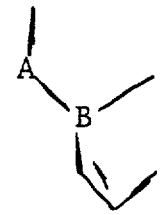 "    should be

-- 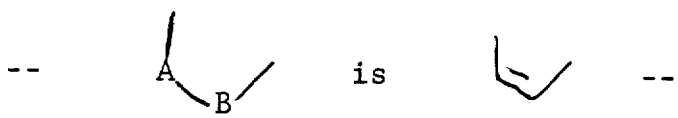 --

Signed and Sealed this

Sixteenth Day of November, 1993

Attest:

BRUCE LEHMAN

Attesting Officer          Commissioner of Patents and Trademarks